(12) United States Patent
Seelig et al.

(10) Patent No.: US 10,633,648 B2
(45) Date of Patent: Apr. 28, 2020

(54) COMBINATORIAL PHOTO-CONTROLLED SPATIAL SEQUENCING AND LABELING

(71) Applicant: University of Washington, Seattle, WA (US)

(72) Inventors: Georg Seelig, Seattle, WA (US); Anna Kuchina, Seattle, WA (US); Alexander B. Rosenberg, Seattle, WA (US)

(73) Assignee: University of Washington, Seattle, WA (US)

( * ) Notice: Subject to any disclaimer, the term of this patent is extended or adjusted under 35 U.S.C. 154(b) by 200 days.

(21) Appl. No.: 15/430,108

(22) Filed: Feb. 10, 2017

(65) Prior Publication Data

US 2017/0233722 A1 Aug. 17, 2017

Related U.S. Application Data

(60) Provisional application No. 62/294,518, filed on Feb. 12, 2016.

(51) Int. Cl.
*C12Q 1/68* (2018.01)
*C12N 15/10* (2006.01)

(52) U.S. Cl.
CPC ..... *C12N 15/1037* (2013.01); *C12N 15/1065* (2013.01); *C12N 15/1068* (2013.01)

(58) Field of Classification Search
None
See application file for complete search history.

(56) References Cited

U.S. PATENT DOCUMENTS

| | | |
|---|---|---|
| 2014/0031243 A1 | 1/2014 | Cai et al. |
| 2016/0253484 A1 | 9/2016 | Fodor et al. |
| 2016/0289740 A1 | 10/2016 | Fu et al. |
| 2016/0304860 A1 | 10/2016 | Hindson et al. |

FOREIGN PATENT DOCUMENTS

| | | |
|---|---|---|
| EP | 2625320 | 8/2013 |
| EP | 2414548 | 10/2015 |
| WO | 2013052101 | 6/2003 |
| WO | 2014110509 | 7/2014 |
| WO | 2015164212 | 10/2015 |

OTHER PUBLICATIONS

Chen, et al., Spatially resolved, highly multiplexed RNA profiling in single cells, Science 348, 412 (2015).
Di Bella, et al., High throughput sequencing methods and analysis for microbiome research, Journal of Microbiological Methods, 2013, 95: 401.
Gschneidtner, et al., A Photolabile Protection Strategy for Terminal Alkynes, Tetrahedron Letters 54,(2013), 5425.
Hutchinson III, et al., DNA sequencing: bench to bedside and beyond, Nucleic Acids Research, 2007, 38 (18): 6227.
Kircher, et al., High-throughput DNA sequencing—concepts and limitations, Bioessays 2010, 32: 524.
Klein, et al., Droplet Barcoding for Single-Cell Transcriptomics Applied to Embryonic Stem Cells, May 21, 2015, Cell 161, 1187-1201.
Lee, et al., Highly Multiplexed Sucellular RNA Sequencing in Situ, Science 343, 1360 (2015).
Lubeck, et al., Single-Cell in Situ RNA Profiling by Sequential Hybridization, Nature Methods 11, 360 (2014).
Lubeck, et al., Single-Cell Systems Biology by Super-Resolution Imaging and Combinatorial Labeling, Nature, Jun. 2012, 9 (7): 743.
Macosko, et al., Highly Parallel Genome-Wide Expression Profiling of Individual Cells Using Nanoliter Droplets, Cell, 161, 1202-1214, May 21, 2015.
Ramil, et al., Photoclick chemistry: a fluorogenic light-triggered in vivo ligation reaction, Current Opinion in Chemical Biology 21 (2014), 21: 89.
Saliba, et al., Single-cell RNA-seq: advances and future challenges, Nucleic Acids Res. 42, 8845-8860, Jul. 22, 2014.
Ikeda, Masato et al., "Chemically Caged Nucleic Acids," Chem. Lett. 46:634-640, 2017.
Liu, Qingyang et al., "Optochemical Control of Deoxyoligonucleotide Function via a Nucleobase-Caging Approach," Accounts of Chemical Research, 47(1):45-55, 2014.
Achim , et al., "High-throughput spatial mapping of single-cell RNA-seq data to tissue of origin", Nature Biotechnology 2015; 33(5): 503-509.
Lovatt , et al., "Transcriptome in vivo analysis (TIVA) of spatially defined single cells in live tissue", Nature Methods 11, 190 (2014).
Satija , et al., "Spatial reconstruction of single-cell gene expression data", Nature Biotechnology 2015; 33(5): 495-502.

*Primary Examiner* — James Martinell
(74) *Attorney, Agent, or Firm* — Christensen O'Connor Johnson Kindness PLLC

(57) ABSTRACT

Methods of labeling or barcoding molecules within one or more portions of a plurality of cells are provided. Kits and systems for labeling or barcoding molecules within one or more portions of a plurality of cells are also provided. The methods, kits, and systems may utilize photo-controlled adapter sequences, nucleic acids tags, and/or linkers.

19 Claims, 20 Drawing Sheets

Specification includes a Sequence Listing.

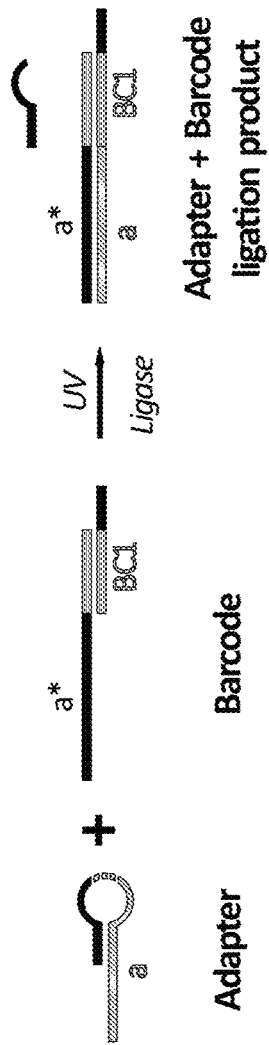
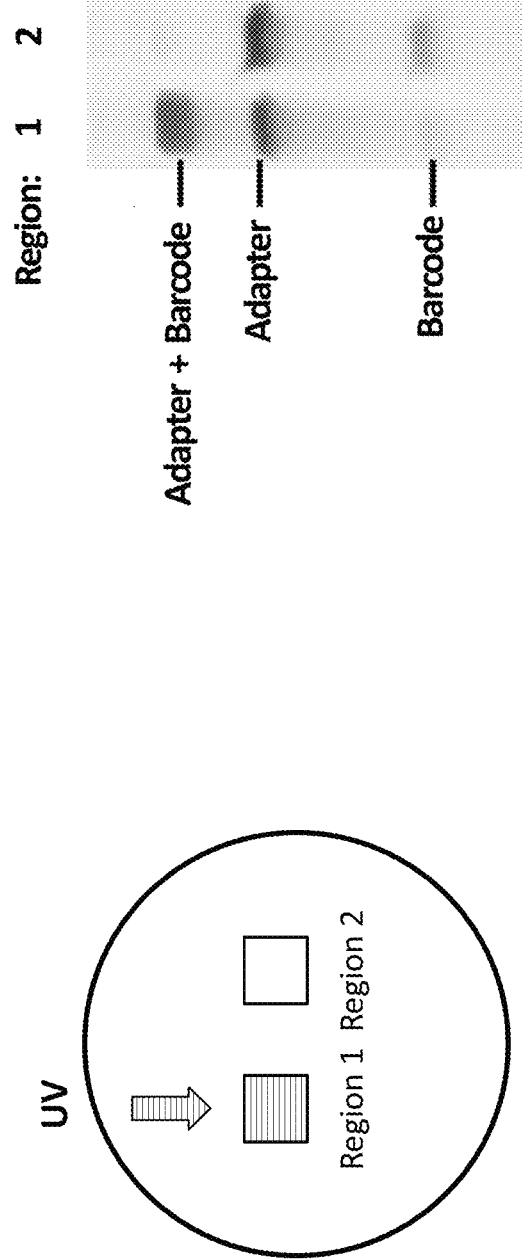
FIG. 15A
FIG. 15B
FIG. 15C

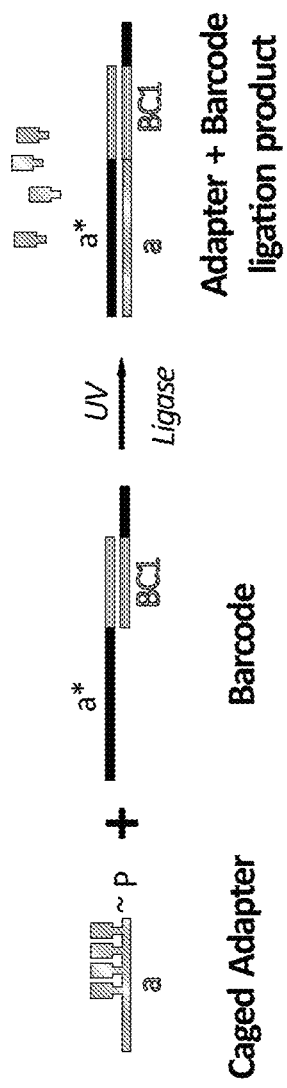
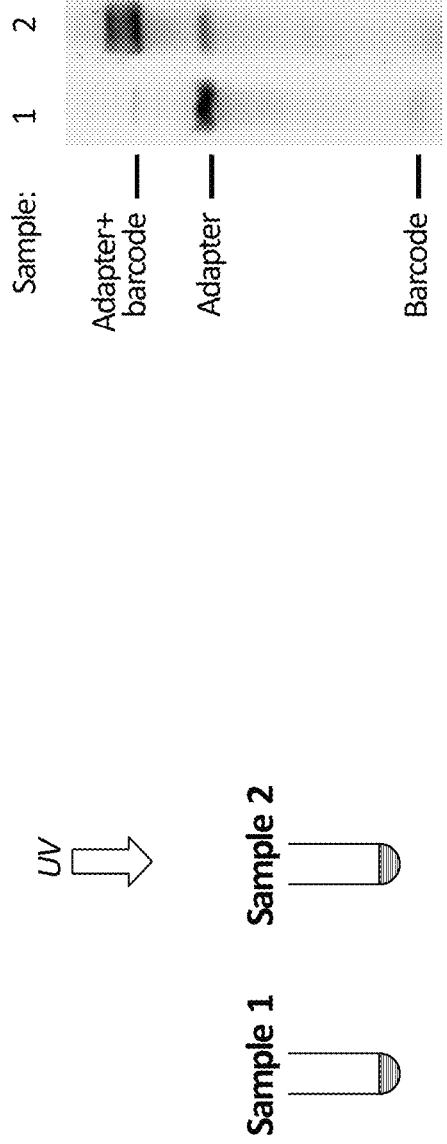
FIG. 16A
FIG. 16B
FIG. 16C

SEQUENCE LISTING

```
<160> NUMBER OF SEQ ID NOS: 12

<210> SEQ ID NO 1
<211> LENGTH: 23
<212> TYPE: DNA
<213> ORGANISM: Artificial Sequence
```

```
<220> FEATURE:
<223> OTHER INFORMATION: Synthetic oligonucleotide

<400> SEQUENCE: 1
gggtgagctt cactgtccat ctg                                              23

<210> SEQ ID NO 2
<211> LENGTH: 52
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Biotin is coupled to the guanine
<220> FEATURE:
<221> NAME/KEY: misc_feature
<222> LOCATION: (28)..(37)
<223> OTHER INFORMATION: n is a, c, g, or t

<400> SEQUENCE: 2
gctgaaccgc tcttccgatc tatcacgnnn nnnnnnncag atggacagtg aa              52

<210> SEQ ID NO 3
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(11)
<223> OTHER INFORMATION: A photocleavable spacer is disposed between the
      adenine and guanine
<220> FEATURE:
<221> NAME/KEY: misc_feature
<222> LOCATION: (35)..(35)
<223> OTHER INFORMATION: n is a, c, g, or t

<400> SEQUENCE: 3
gtgagcaaaa gctcacccct tttttttttt tttvn                                 35

<210> SEQ ID NO 4
<211> LENGTH: 46
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Biotin is coupled to the guanine
<220> FEATURE:
<221> NAME/KEY: misc_feature
<222> LOCATION: (22)..(31)
<223> OTHER INFORMATION: n is a, c, g, or t

<400> SEQUENCE: 4
gctgaaccgc tcttccgatc tnnnnnnnnn ncagatggat cacgtt                     46

<210> SEQ ID NO 5
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 5
gggtgagcaa cgtgatccat ctg                                              23
```

```
<210> SEQ ID NO 6
<211> LENGTH: 46
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Biotin is coupled to the guanine
<220> FEATURE:
<221> NAME/KEY: misc_feature
<222> LOCATION: (22)..(31)
<223> OTHER INFORMATION: n is a, c, g, or t

<400> SEQUENCE: 6
gctgaaccgc tcttccgatc tnnnnnnnnn ncagatggga tcagcg            46

<210> SEQ ID NO 7
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 7
gggtgagccg ctgatcccat ctg                                     23

<210> SEQ ID NO 8
<211> LENGTH: 33
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(11)
<223> OTHER INFORMATION: A photocleavable spacer is disposed between the
      adenine and guanine

<400> SEQUENCE: 8
gtgagcaaaa gctcacccca gatggatcac gtt                          33

<210> SEQ ID NO 9
<211> LENGTH: 33
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(11)
<223> OTHER INFORMATION: A photocleavable linker is disposed between the
      adenine and guanine

<400> SEQUENCE: 9
gtgagcaaaa gctcacccca gatgggatca gcg                          33

<210> SEQ ID NO 10
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: A terminal phosphate is coupled to the cytosine
<220> FEATURE:
```

```
<221> NAME/KEY: misc_feature
<222> LOCATION: (2)..(2)
<223> OTHER INFORMATION: The thymine is NPOM-caged
<220> FEATURE:
<221> NAME/KEY: misc_feature
<222> LOCATION: (4)..(4)
<223> OTHER INFORMATION: The thymine is NPOM-caged
<220> FEATURE:
<221> NAME/KEY: misc_feature
<222> LOCATION: (6)..(6)
<223> OTHER INFORMATION: The thymine is NPOM-caged
<220> FEATURE:
<221> NAME/KEY: misc_feature
<222> LOCATION: (8)..(8)
<223> OTHER INFORMATION: The thymine is NPOM-caged
<220> FEATURE:
<221> NAME/KEY: misc_feature
<222> LOCATION: (24)..(24)
<223> OTHER INFORMATION: n is a, c, g, or t

<400> SEQUENCE: 10
ctctgtcttt ttttttttt ttvn                                           24

<210> SEQ ID NO 11
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 11
ctggtatgac aacgaatttg gc                                            22

<210> SEQ ID NO 12
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 12
cagacgtgtg ctcttccgat ct                                            22
```

COMBINATORIAL PHOTO-CONTROLLED SPATIAL SEQUENCING AND LABELING

CROSS-REFERENCE TO RELATED APPLICATIONS

This application claims the benefit of U.S. Provisional Application No. 62/294,518, filed Feb. 12, 2016, which is hereby incorporated by reference in its entirety.

STATEMENT AS TO RIGHTS TO INVENTIONS MADE UNDER FEDERALLY SPONSORED RESEARCH OR DEVELOPMENT

This invention was made with government support under Grant No. R01 CA207029, awarded by the National Institutes of Health, and Grant No. CCF-1317653, awarded by the National Science Foundation. The government has certain rights in the invention.

TECHNICAL FIELD

The present disclosure relates generally to methods of labeling or barcoding molecules within one or more portions of a plurality of cells. The present disclosure also relates to kits and systems for labeling or barcoding molecules within one or more portions of a plurality of cells. In particular, the methods, kits, and systems may utilize photo-controlled adapter sequences, nucleic acids tags, and/or linkers.

BACKGROUND

Characterizing gene expression at the single cell level can assist in understanding biological phenomena from development to cancer. Recent work has begun to address characterization of gene expression at the single cell level and has demonstrated several high-throughput methods for sequencing individual cells (see E. Z. Macosko, et al., Cell 161, 1202 (2015) and A. M. Klein, et al., Cell 161, 1187 (2015)). However, existing high-throughput single-cell sequencing methods do not generally preserve information about the spatial arrangement of cells in their original biological context. Thus, these methods may provide an incomplete picture of gene expression in complex multicellular systems.

Single-molecule fluorescence in situ hybridization (smFISH) techniques can be used to reveal RNA expression profiles in individual cells. Recent work has demonstrated that single-molecule RNA FISH can be used to sequentially label and image hundreds of mRNAs in individual cells (see E. Lubeck, et al., Nature Methods 11, 360 (2014); K. H. Chen, et al., Science 348, 412 (2015); and J. R. Moffitt, et al., PNAS 113(39), 11046 (2016)). However, smFISH may only reveal mRNAs for which specific sequences were designed, while sequencing can be used to measure the levels of all RNA present in the cell, even those with unexpected mutations or truncations. Moreover, smFISH techniques may not be likely to scale to the very large numbers of cells and transcripts that can be assayed with next generation sequencing.

Microdissection methods, such as laser capture microdissection, can be used for sequencing spatially defined groups of cells. However, this approach can require physical separation of the cells of interest and is not very high throughput. A recent study utilized a custom made oligonucleotide array to achieve high coverage gene expression measurements in tissue sections with spatial resolution. However, this strategy utilizes manufacture of a special array for every single measurement, the spatial resolution is determined by the array features, and this strategy does not scale to three-dimensional spatial mapping of tissue (see P. L. Stahl, et al., Science 353(6294), 78 (2016)).

BRIEF DESCRIPTION OF THE DRAWINGS

The embodiments disclosed herein will become more fully apparent from the following description and appended claims, taken in conjunction with the accompanying drawings.

FIG. 15A depicts one round of an embodiment of in vitro barcode ligation.

FIG. 15B depicts a schematic of an experiment wherein both wells of a plate contain the same nucleic acid species and well 1 is exposed with 405 nm light.

FIG. 15C is an image of a polyacrylamide gel showing the appearance of a ligation product in well 1 of FIG. 15B.

FIG. 16A depicts one round of an embodiment of in vitro barcode ligation to a photocaged adapter.

FIG. 16B is a schematic of an experiment wherein both test tubes contain the same nucleic acid species and Sample 2 is exposed to UV light via a transilluminator.

FIG. 16C depicts a polyacrylamide gel showing the appearance of a ligation product (adaptor+barcode) in Sample 2.

DETAILED DESCRIPTION

The present disclosure relates generally to methods of labeling or barcoding molecules within one or more portions of a plurality of cells. The present disclosure also relates to kits and systems for labeling or barcoding molecules within one or more portions of a plurality of cells. In particular, the methods, kits, and systems may utilize photo-controlled adapter sequences, nucleic acids tags, and/or linkers.

Figure 1:
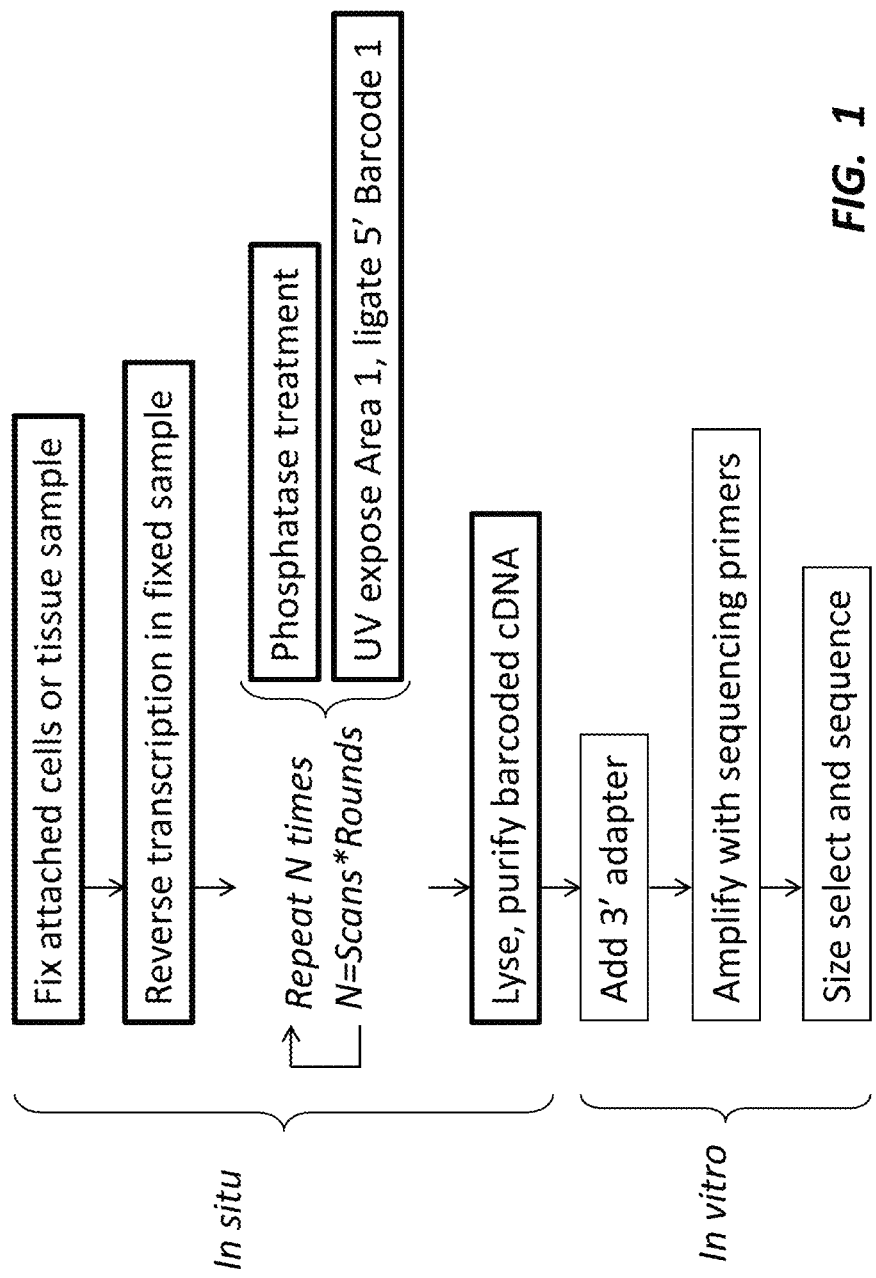
FIG. 1 depicts a high-level work flow of labeling methods according to some embodiments of the present disclosure.

High-throughput labeling methods that can provide information about the spatial organization of cells in their original context are provided herein. These methods can provide information useful in sequencing and other applications where there are, or may be, spatially different expression of, for example, RNAs within cells in a sample. FIG. 1 depicts a high-level work flow of the labeling methods according to some embodiments of the present disclosure.

It will be readily understood that the embodiments, as generally described herein, are exemplary. The following more detailed description of various embodiments is not intended to limit the scope of the present disclosure, but is merely representative of various embodiments. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified.

The term "binding" is used broadly throughout this disclosure to refer to any form of attaching or coupling two or more components, entities, or objects. For example, two or more components may be bound to each other via chemical bonds, covalent bonds, ionic bonds, hydrogen bonds, electrostatic forces, Watson-Crick hybridization, etc.

A first aspect of the disclosure relates to methods of labeling molecules within one or more portions or regions of a plurality of cells. For example, the methods may include labeling molecules within one of more regions of a cell culture sample, a tissue sample, a model organism, or another suitable plurality of cells. In various embodiments, the method may be a high-throughput labeling method that provides, or that is configured to provide, information about spatial organization of the plurality of cells (e.g., in their original context).

The samples may include tissues and/or cells that are fixed in a particular location. In such samples, there may be spatially differential expression of RNA for which the methods of the present disclosure may be useful. In certain embodiments, the samples may be substantially two-dimensional samples (e.g., tissues slices). In certain other embodiments, the samples may be three-dimensional samples.

In some embodiments, the methods may include: (a) coupling at least one photo-controlled adapter sequence to molecules within the plurality of cells; (b) exposing a first portion of the plurality of cells to photonic energy (e.g., light) to activate the at least one photo-controlled adapter sequence within the first portion of the plurality of cells; (c) providing primary nucleic acid tags to the plurality of cells; (d) coupling the activated photo-controlled adapter sequences within the first portion of the plurality of cells with the provided primary nucleic acid tags; (e) exposing a second portion of the plurality of cells to photonic energy to activate the at least one photo-controlled adapter sequence and/or the primary nucleic acid tags within the second portion of the plurality of cells; (f) providing secondary nucleic acid tags to the plurality of cells; and/or (g) coupling the activated photo-controlled adapter sequence and/or the activated primary nucleic acid tags within the second portion of the plurality of cells with the provided secondary nucleic acid tags.

In certain embodiments, the methods may include repeating steps (b), (c), and/or (d) with subsequent (e.g., tertiary, quaternary, etc.) nucleic acid tags and/or within subsequent (e.g., third, fourth, etc.) portions or regions of the plurality of cells. In various embodiments, steps (b), (c), and/or (d) can be repeated prior to step (e) with primary nucleic acid tags having different barcode domains (or barcode sequences). Steps (b), (c), and/or (d) may be repeated a number of times sufficient to generate a unique series of nucleic acid tags for the molecules within a specific portion of the plurality of cells. The number of times may be selected from 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, or another suitable number of times.

In various embodiments, the methods may further include: (h) repeating steps (e), (f), and/or (g) with subsequent nucleic acid tags and/or within subsequent portions of the plurality of cells, wherein step (g) may include: i) coupling the activated photo-controlled adapter sequence and/or the activated primary nucleic acid tags within the second portion of the plurality of cells with the provided secondary nucleic acid tags, ii) coupling the activated photo-controlled adapter sequence, and/or the activated primary nucleic acid tags, and/or the activated secondary nucleic acid tags within a third portion of the plurality of cells with provided tertiary nucleic acid tags, and/or iii) coupling the activated photo-controlled adapter sequence, and/or the activated primary nucleic acid tags, and/or the activated subsequent (e.g., secondary, tertiary, quaternary, etc.) nucleic acid tags within a subsequent (e.g., second, third, fourth, etc.) portion of the plurality of cells with provided subsequent nucleic acid tags.

For example, step (h) may be repeated a number of times sufficient to generate a unique series of nucleic acid tags for the molecules within a specific portion or region of the plurality of cells. The number of times may be selected from 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, or another suitable number of times. Furthermore, the majority of the nucleic acid tag-bound nucleic acids from the specific portion of the plurality of cells may comprise the same series of bound nucleic acid tags.

In some other embodiments, the methods may include: (a) coupling at least one photo-controlled adapter sequence to molecules within the plurality of cells; (b) exposing a first portion of the plurality of cells to photonic energy (e.g., light) to activate the at least one photo-controlled adapter sequence within the first portion of the plurality of cells; (c) providing primary nucleic acid tags to the plurality of cells; (d) coupling the activated photo-controlled adapter sequences within the first portion of the plurality of cells with the provided primary nucleic acid tags; (e) exposing a subsequent (e.g., second, third, fourth, etc.) portion of the plurality of cells to photonic energy to activate the at least one photo-controlled adapter sequence and/or the primary nucleic acid tags within the subsequent (e.g., second, third, fourth, etc.) portion of the plurality of cells; (f) providing subsequent (e.g., secondary, tertiary, quaternary, etc.) nucleic acid tags to the plurality of cells; and/or (g) coupling the activated photo-controlled adapter sequence and/or the activated primary nucleic acid tags within the subsequent (e.g., second, third, fourth, etc.) portion of the plurality of cells with the provided subsequent nucleic acid tags.

In certain other embodiments, the methods may include repeating steps (b), (c), and/or (d) with subsequent nucleic acid tags and/or within subsequent portions or regions of the plurality of cells. In various embodiments, steps (b), (c), and/or (d) can be repeated prior to step (e) with primary nucleic acid tags having different barcode domains (or barcode sequences). Steps (b), (c), and/or (d) may be repeated a number of times sufficient to generate a unique series of nucleic acid tags for the molecules within a specific portion of the plurality of cells. The number of times may be selected from 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, or another suitable number of times.

In various other embodiments, the methods may further include: (h) repeating steps (e), (f), and/or (g) with subsequent nucleic acid tags and/or within subsequent portions of the plurality of cells, wherein step (g) may include: i) coupling the activated photo-controlled adapter sequence and/or the activated primary nucleic acid tags within the subsequent portion of the plurality of cells with the provided subsequent nucleic acid tags and/or ii) coupling the activated photo-controlled adapter sequence and/or the activated primary nucleic acid tags, and/or the activated subsequent nucleic acid tags within a subsequent portion of the plurality of cells with provided subsequent nucleic acid tags.

For example, step (h) may be repeated a number of times sufficient to generate a unique series of nucleic acid tags for the molecules within a specific portion or region of the plurality of cells. The number of times may be selected from 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, or another suitable number of times. Furthermore, the majority of the nucleic acid tag-bound nucleic acids from the specific portion of the plurality of cells may comprise the same series of bound nucleic acid tags.

In certain embodiments, the number of portions (or regions) in a first round corresponds to the number of first-round exposures to photonic energy, which corresponds to the number of unique primary nucleic acid tags (having different barcode domains). The number of portions (or regions) in a second round corresponds to the number of second-round exposures to photonic energy, which corresponds to the number of unique secondary nucleic acid tags (having different barcode domains). The methods can continue for n rounds. For example, the maximum number of combinatorial labeled portions (or regions) after n rounds can equal the number of first-round portions/distinct barcodes multiplied by the number of second-round portions/distinct barcodes and further multiplied by the number of n-round portions/distinct barcodes. Stated another way, the maximum number of combinatorial labeled regions after n rounds=the # of first-round regions/distinct barcodes×the # of second-round regions/distinct barcodes× . . . ×the # of n-round regions/distinct barcodes. For example, 3 rounds with 4 photonic energy (or light) exposure/ligations each: 4×4×4=64 labeled portions (or regions).

In some embodiments, the methods may further include treating the plurality of cells with an agent that deactivates the photo-controlled adapter sequence prior to step (b). In some other embodiments, the methods may include: identifying a portion of the plurality of cells having molecules that are not to be labeled; exposing the identified portion of the plurality of cells to photonic energy (i.e., prior to step (b)); and/or treating the plurality of cells with an agent that deactivates the photo-controlled adapter sequence. The agent may be at least one of a phosphatase, a specific oligonucleotide (wherein the specific oligonucleotide is to be filtered out during post-processing), a blocking oligonucleotide having a higher binding energy to the photo-controlled adapter sequence than the nucleic acid tags, an enzyme that specifically destroys or modifies an uncaged sequence, a protein that binds to an exposed specific protein binding site, or another suitable agent.

Depending on the mechanism of barcode or nucleic acid tag strand attachment to the photo-controlled adapter sequence, various deactivating agents may be used to destroy or de-activate the photo-controlled adapter sequence in the region of a sample not intended for barcoding. If the photo-controlled adapter sequence is to be coupled to the barcode strands by ligation after exposing the end phosphate, a pre-processing step can be performed that involves treatment with a phosphatase enzyme immediately after activating the photo-controlled adapter sequence in an off-target region. In some embodiments, the phosphatase may be heat-sensitive (e.g., Antarctic phosphatase from NEB™), in which case its activity can be subsequently switched off by subjecting the sample to an elevated temperature for a specified duration. Otherwise, the phosphatase enzyme may be removed simply by washing or by a combination of these methods.

Both in the case of using a photocleavable adapter sequence or a photocaged adapter sequence, a specifically selected barcode may be coupled to the molecules within the off-target region to be filtered from the data during post-processing and analysis. Another option may be to use a blocking oligonucleotide specifically designed to have a higher binding energy to the activated photo-controlled adapter sequence than that of the barcode strands. In such an embodiment, the binding of the blocking oligonucleotide can prevent the barcode strands from attachment in the off-target region.

Alternatively, when using a photocaged adapter sequence, the deactivating agent may be an enzyme (e.g., a restriction endonuclease, Cas9 nuclease, etc.), which specifically destroys the exposed uncaged photocaged adapter sequence. Other DNA-modifying agents may also be used to irreversibly modify an exposed photocaged adapter sequence in such a way that the attachment of the barcode strands is inhibited or prevented. For a click chemistry barcode addition strategy, the deactivating agent may remove or modify the unmasked 5'-terminal alkyne on the activated photocaged adapter sequence. Additionally, the exposed photocaged adapter sequence may include a specific protein binding site for which a binding protein may be used as a deactivating agent by occluding the site from the barcode strands.

The photo-controlled adapter sequence may be a photocaged adapter sequence, a photocleavable adapter sequence, or another suitable photo-controlled adapter sequence. In various embodiments wherein the photo-controlled adapter sequence is a photocaged adapter sequence, the photocaged adapter sequence may include a hybridization domain. Furthermore, the hybridization domain may include one or more photocaged nucleic acids. In certain embodiments, the photocaged adapter sequence may include a terminal phosphate.

Additionally, in some embodiments wherein the photo-controlled adapter sequence is a photocaged adapter sequence, each or at least a portion of the primary nucleic acid tags may include a domain at least partially complementary to the hybridization domain and/or a primary barcode domain. Each or at least a portion of the secondary nucleic acid tags may include a secondary barcode domain and/or a domain at least partially complementary to one of the primary barcode domain or a secondary barcode domain of a different secondary nucleic acid tag. Furthermore, subsequent (e.g., tertiary, quaternary, etc.) nucleic acid tags may include a subsequent barcode domain and/or a domain at least partially complementary to one of the primary barcode domain, the secondary barcode domain, or a subsequent barcode domain of a different subsequent nucleic acid tag. In certain embodiments, at least one of the nucleic acid tags may be a photo-controlled nucleic acid tag. For example, one or more of the nucleic acid tags may include a photocleavable linker. In various embodiments, at least one of the nucleic acid tags may include a capture agent.

In some embodiments, a barcode domain may be about one nucleotide to about 25 nucleotides, about two nucleotides to about 20 nucleotides, about four nucleotides to about 15 nucleotides, about six nucleotides to about 10 nucleotides, about eight nucleotides, or another suitable number of nucleotides. The barcode nucleic acid molecule for a region may be unique to that region. Multiple rounds of barcodes can be appended to molecules present in the plurality of cells. In certain embodiments, each round of barcode nucleic acid molecules can include a different barcode domain. Accordingly, the nucleic acid molecules in the sample can be labeled combinatorially, wherein each subsequent round of labeling provides a new barcode domain.

In certain embodiments, wherein the photo-controlled adapter sequence is a photocleavable adapter sequence, the photocleavable adapter sequence may include a hybridization domain, a domain at least partially complementary to the hybridization domain, and/or a photocleavable linker coupling the hybridization domain and the domain at least partially complementary to the hybridization domain.

Additionally, in various embodiments wherein the photo-controlled adapter sequence is a photocleavable adapter sequence, each or at least a portion of the primary nucleic acid tags may include a domain complementary or at least partially complementary to the hybridization domain and/or a primary barcode domain. Each or at least a portion of the secondary nucleic acid tags may include a secondary barcode domain at least partially complementary to one of the primary barcode domain or a secondary barcode domain of a different secondary nucleic acid tag, a secondary hybridization domain, a domain at least partially complementary to the secondary hybridization domain, and/or a photocleavable linker coupling the secondary hybridization domain and the domain at least partially complementary to the secondary hybridization domain. Furthermore, subsequent (e.g., tertiary, quaternary, etc.) nucleic acid tags may include a subsequent barcode domain at least partially complementary to one of the primary barcode domain, a secondary barcode domain, or a subsequent barcode domain of a different subsequent nucleic acid tag, a subsequent hybridization domain, a domain at least partially complementary to the subsequent hybridization domain, and/or a photocleavable linker coupling the subsequent hybridization domain and the domain at least partially complementary to the subsequent hybridization domain. In various embodiments, at least one of the nucleic acid tags may include a capture agent.

In some embodiments, at least one of the photocleavable adapter sequence, the primary nucleic acid tags, and/or the secondary nucleic acid tags may include one or more photocleavable linkers. For example, the photocleavable adapter sequence may include two photocleavable linkers. In some other embodiments, at least one of the photocleavable adapter sequence, the primary nucleic acid tags, and/or the secondary nucleic acid tags may include two or more photocleavable linkers. It may be useful to include multiple photocleavable linkers, for example, to increase specificity and/or to reduce spurious ligation events from background photonic energy. For example, if a photo-controlled adapter sequence includes two photocleavable linkers it may be less likely that the photo-controlled adapter sequence will be cleaved when not part of the region exposed to photonic energy. A percentage of photocleavable linkers may be cleaved when not exposed to photonic energy, thereby unintentionally exposing a hybridization domain. However, if the photo-controlled adapter sequence includes two or more photocleavable linkers, each of the two or more photocleavable linkers would need to be cleaved before the hybridization domain would be exposed. This is less likely to occur with two photocleavable linkers than with one photocleavable linker.

Figure 2:
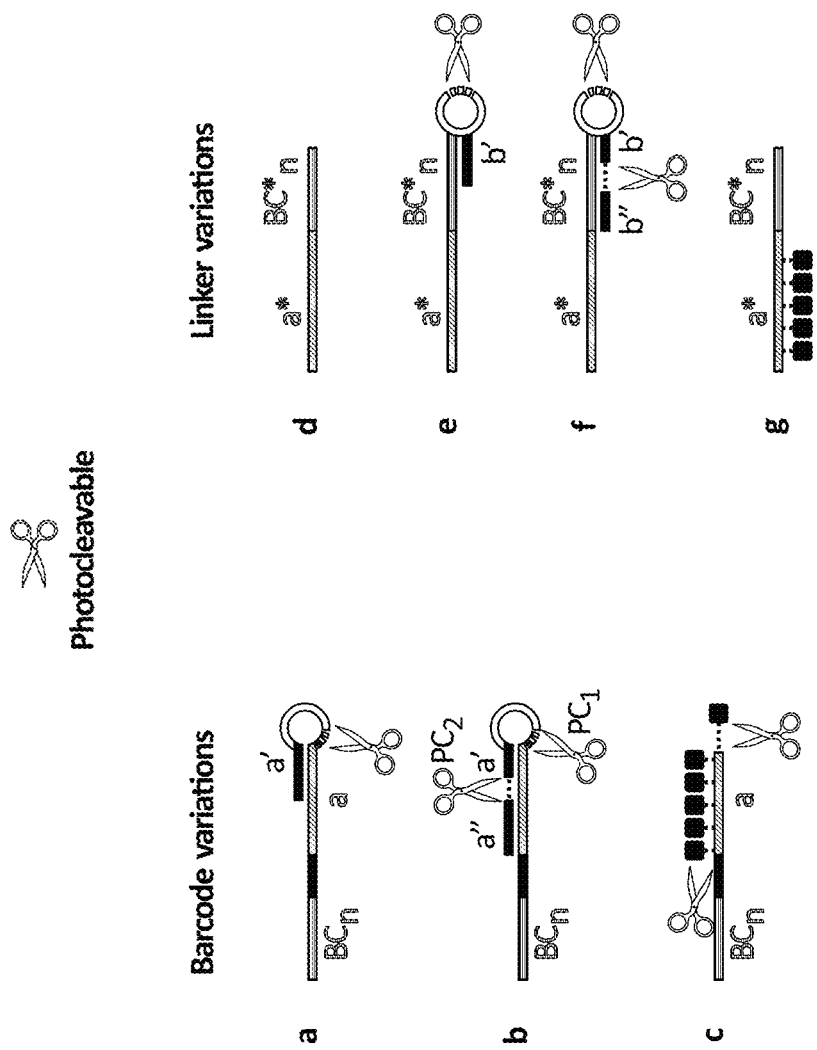
FIG. 2A is schematic illustration of a barcode nucleic acid sequence including a single photocleavable linker, in accordance with an embodiment of the present disclosure.
FIG. 2B is schematic illustration of a barcode nucleic acid sequence including two photocleavable linkers, in accordance with an embodiment of the present disclosure.
FIG. 2C is schematic illustration of a barcode nucleic acid sequence including a plurality of photocleavable linkers, in accordance with an embodiment of the present disclosure.
FIG. 2D is schematic illustration of a linker nucleic acid sequence, in accordance with an embodiment of the present disclosure.
FIG. 2E is schematic illustration of a linker nucleic acid sequence including a photocleavable linker, in accordance with an embodiment of the present disclosure.
FIG. 2F is schematic illustration of a linker nucleic acid sequence including two photocleavable linkers, in accordance with an embodiment of the present disclosure.
FIG. 2G is schematic illustration of a linker nucleic acid sequence including a plurality of photocleavable linkers, in accordance with an embodiment of the present disclosure.

In certain embodiments, the photocleavable linker may be a molecule, a portion of a nucleic acid tag, and/or a portion of a photo-controlled adapter sequence. The photocleavable linker may break apart as a result of exposure to photonic energy. In various embodiments, the photocleavable linker may be a non-nucleosidic moiety that can be used to link two nucleotide sequences through a short, photo-cleavable spacer arm. The photocleavable linker may be added at any position of a nucleic acid molecule. Photocleavage of the photocleavable linker by photonic energy may yield one 5'-phosphorylated oligo and one 3'-phosphorylated oligo. In some embodiments, the photocleavable linker may include 1-(2-nitrophenyl) ethyl or another suitable compound. Examples of barcode nucleic acid molecules including one and two or more photocleavable linkers are depicted in FIG. 2.

In certain embodiments, the first portion and the second portion of the plurality of cells may be partially overlapping, substantially overlapping, or identical. For example, the first portion may be the same as the second portion. In certain other embodiments, the first portion and the second portion of the plurality of cells may not have any cells in common. In various embodiments, at least one of the first portion and the second portion of the plurality of cells may be noncontiguous. For example, the first portion may include two regions that are not adjacent to each other. Furthermore, at least one of the first portion and the second portion of the plurality of cells may include only a portion of a cell.

In some embodiments, methods of labeling molecules within one or more portions of a plurality of cells may include fixing and/or permeabilizing at least a portion of the plurality of cells prior to step (a). The methods may also include lysing at least a portion of the plurality of cells. Such lysing may release one or more of the molecules from within the plurality of cells. In certain embodiments, the methods may include coupling at least two of the nucleic acid tags that are bound to the released molecules. Such coupling may be performed via ligation, template switching, or another suitable method of coupling. In various embodiments, the methods may include generating complementary DNAs (cDNAs) within at least a portion of the plurality of cells. Furthermore, the methods may include removing unbound nucleic acid tags.

Figure 3:
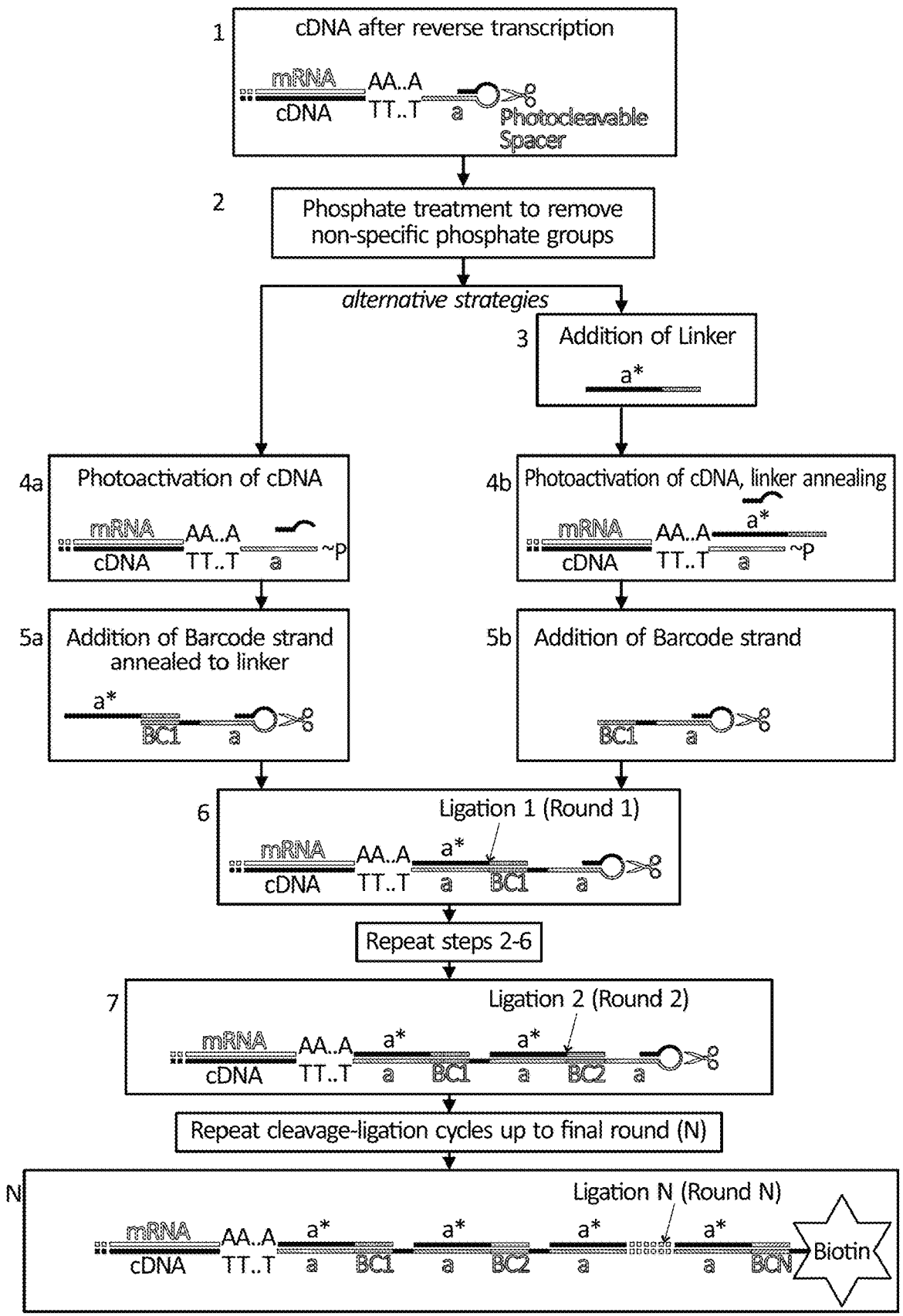
FIG. 3 depicts two embodiments of a photoactivation labeling scheme.
Figure 4:
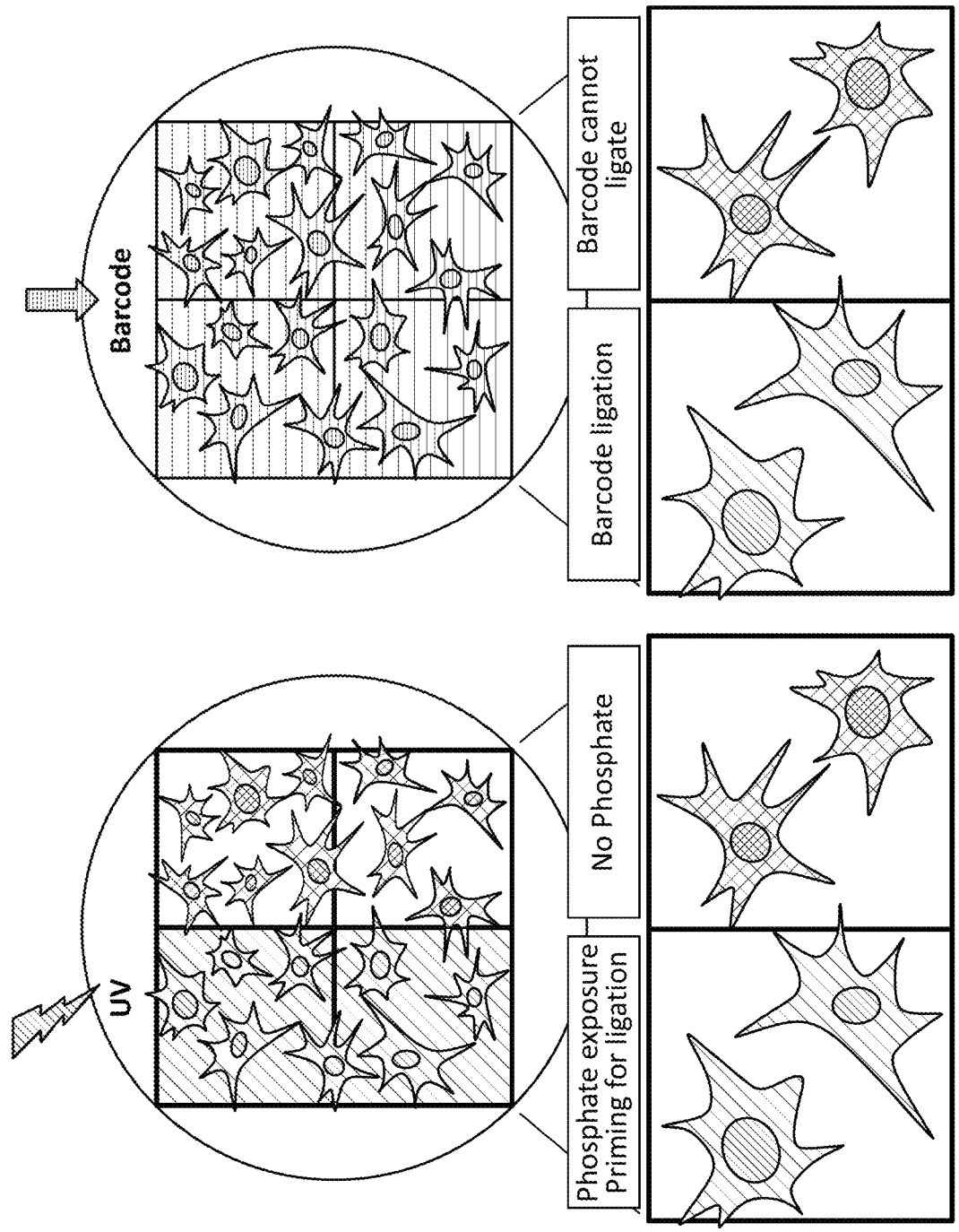
FIG. 4 depicts labeling two spatially distinct regions of a sample with different barcode molecules.

In various embodiments, a ligase enzyme may be added to the sample to ligate adjacent uncoupled nucleic acid molecules (see FIG. 3, step 6 and FIG. 4, right). Since the ligation reaction may utilize a 5' phosphate, cDNA in a previously exposed ROI can be covalently coupled to a barcode nucleic acid molecule or photo-controlled adapter sequence. Ligation may be useful where the nucleic acid molecules in a sample are to be sequenced. By ligating the labeled molecules, they can be sequenced and, if a region has been associated with the one or more barcode nucleic acid molecules, a user can determine where those nucleic acid molecules were in a sample prior to lysing and sequencing.

Other methods may also be used to facilitate the attachment of the barcodes (i.e., methods other than DNA ligase-mediated ligation). For example, terminal alkynes can be protected by a photolabile masking group based on a combination of the photoactive o-nitrobenzyl (NB) group and tertiary propargyl ethers. The combined NB-propargyl ether groups are generally stable under strong alkaline conditions but can release terminal alkynes after UV irradiation under alkaline conditions. Terminal alkynes are reactive species in the 1,3-dipolar cycloaddition between azides and alkynes to give 1,2,3-triazoles (click-chemistry) (see T. A. Gschneidtner, et al., Tetrahedron Letters 54, 40 (2013)). This click reaction could be employed for coupling the barcode (e.g., carrying an azide at the 3'-end) to the cDNA-adapter 5' end carrying a photosensitively masked terminal alkyne.

Further methods may include utilizing photoinduced tetrazole-alkene cycloaddition, also termed "photoclick chemistry," that can offer a chemical ligation platform for in vivo reactions (see C. P. Ramil, et al., Current Opinion in Chemical Biology 21, 89 (2014)). In this method, a user can couple a tetrazole ring to the 5' end of an RT primer and/or a barcode nucleic acid molecule as provided herein and the user can couple an alkene group to the 3' end of a next-round barcode oligo. The tetrazole to nitrile imine conversion can be triggered with a UV lamp, LED light, and/or laser beam due to the high quantum efficiency of the photoinduced tetrazole ring rupture. A 405 nm laser-activatable terthiophene-tetrazole has been designed. Also, aphthalene-tetrazoles may be activated by a near 700 nm laser, thus presenting a suitable strategy for two-photon activation of the barcoding region inside a 3-dimensional sample.

In various embodiments, methods of labeling nucleic acids in a region of a plurality of cells may include fixing and/or permeabilizing the plurality of cells. In some embodiments, the cells and/or the tissues being analyzed can be fixed and/or permeabilized prior to coupling a photo-controlled adapter sequence to the nucleic acid molecule or generating cDNAs. For example, components of a cell may be fixed or cross-linked such that the components are immobilized or held in place. The plurality of cells may be fixed using any suitable method. In some embodiments the plurality of cells may be fixed using: formaldehyde in phosphate buffered saline (PBS) (e.g., in about 4% formaldehyde in PBS), methanol (e.g., at about −20° C.), ethanol (e.g., 70-100% ethanol at about −20° C. or about room temperature), acetic acid (e.g., at about −20° C.), Carnoy's solution (e.g., at about −20° C.), methacarn (e.g., at about −20° C.), or acetone (e.g., at about −20° C.).

In certain embodiments, the methods of labeling nucleic acids in a first cell may include permeabilizing a plurality of cells. Stated another way, holes or openings may be formed in outer membranes of the plurality of cells. TRITON™ X-100 may be added to the plurality of cells, followed by the addition of HCl to form the one or more holes. About 0.2% TRITON™ X-100 may be added to the plurality of cells, for example, followed by the addition of about 0.1 N HCl. In some embodiments, cells can be permeabilized in about 70% ethanol, about 100% methanol, about 0.2% Tween-20, and/or about 0.1% NP-40.

As stated above, the plurality of cells may be selected from a whole or at least a portion of at least one of a mammal, a plant, a *Danio* species (e.g., *Danio rerio*), a *Drosophila* species (e.g., *Drosophila melanogaster*), a *Caenorhabditis* species (e.g., *Caenorhabditis elegans*), and a bacterium. For example, the methods may be used on whole organisms (e.g., model organisms). In some embodiments, the plurality of cells may be substantially two-dimensional (e.g., a tissue slice). In some other embodiments, the plurality of cells may be three-dimensional.

To activate a specific region within a thick, three-dimensional sample, two-photon microscopy may be used to cleave a specifically designed two-photon illumination-compatible photocleavable spacer. While UV and violet light can have limited tissue penetration, two-photon excitation techniques can permit deeper sample penetration (e.g., up to 8 mm in bovine muscle tissue) without damaging the tissue. Under two-photon irradiation conditions, a molecule having an absorbance maximum at 350 nm can be excited by simultaneously absorbing two photons of precisely half the energy, i.e., 700 nm. Due to a very small efficient excitation volume, a very precise region within a sample can be selected. Recently, a two-photon caged phosphoramidite (3-nitro-2-ethyldibenzofuran) suitable for coupling to DNA nucleotides was described (see H. Lusic, et al., Organic Letters, 12 (5), 916 (2010)). In some embodiments, this variety of photocleavable spacer may be used instead of a UV-cleavable linker.

The molecules may be selected from at least one of RNA, cDNA, DNA, protein, peptide, antigen, or another suitable molecule. In some embodiments wherein the molecules are RNA, the photo-controlled adapter sequence may be a single-stranded nucleic acid molecule and step (a) may include one of ligating a 5' end of the single-stranded nucleic acid molecule to a 3' end of the RNA or ligating a 3' end of the single-stranded nucleic acid molecule to a 5' end of the RNA. In certain embodiments, step (a) may include hybridizing the photo-controlled adapter sequence to the RNA.

In various embodiments wherein the molecules are DNA, the method may further include digesting at least a portion of the DNA prior to step (a). Furthermore, step (a) may include ligating the photo-controlled adapter sequence to the digested DNA. In some embodiments, step (a) may include coupling the photo-controlled adapter sequence to the DNA by integrating the photo-controlled adapter sequence into the DNA using a transposase and releasing the transposase to expose the photo-controlled adapter sequence.

In certain embodiments wherein the molecules are protein, peptide, and/or antigen, the photo-controlled adapter sequence may be coupled to a unique identifier sequence that is coupled to an antibody, the unique identifier sequence configured to uniquely identify the antibody. Furthermore, step (a) may include coupling the antibodies comprising the photo-controlled adapter sequence and the unique identifier sequence to the protein, peptide, and/or antigen. In various embodiments, the photo-controlled adapter sequence may be integrated in an aptamer and step (a) may include coupling the aptamer to the protein, peptide, and/or antigen.

A variety of photo-caging groups have been characterized. These include, but are not limited to, derivatives of nitrobenzyl such as nitrophenyl (NP,) α-carboxy-2-nitrobenzyl (CNB), 1-(2-nitrophenyl)ethyl (NPE), 4,5-dimethoxy-2-nitrobenzyl (DMNB), 1-(4,5-dimethoxy-2-nitrophenyl) ethyl (DMNPE), and 5-carboxymethoxy-2-nitrobenzyl (CMNB) (see G. C. R. Ellis-Davies, Nature Methods 4, 619 (2007) and G. Bort, et al., Angewandte Chemie 52, 17, 4526 (2013)). Coumarin-derived caging groups, such as 6-bromo-7-hydroxycoumarin-4-methyl (Bhc) (see T. Furuta, et al., PNAS 96(4), 1193 (1999)) and 8-bromo-7-hydroxyquinoline (BHQ) (see Y. Zhu, et al., JACS 128(13), 4267 (2006)), may also have potential for 2-photon activation.

Terminal alkynes can be protected by a photolabile masking group based on a combination of the photoactive o-nitrobenzyl (NB) group and tertiary propargyl ethers. The combined NB-propargyl ether groups are generally stable under strong alkaline conditions but release terminal alkynes after UV irradiation under alkaline conditions. Terminal alkynes are reactive species in a number of important chemical reactions such as the 1,3-dipolar cycloaddition between azides and alkynes to give 1,2,3-triazoles (click-chemistry). This click reaction may be employed for coupling the barcode, for example, carrying an azide at the 3'-end, to the cDNA-adapter 5' end carrying a photo-masked terminal alkyne (see T. A. Gschneidtner, et al., Tetrahedron Letters 54(40), 5426 (2013)) using a short oligonucleotide called a "splint" to bring them together.

A photolabile group, 6-nitropiperonyloxymethyl (NPOM), may be coupled to the N3 position of thymidine, impairing base-pairing properties and thus hindering hybridization of complementary oligonucleotides (see D. D. Young, et al., Organic and Biomolecular Chemistry 5, 999 (2007) and A. Deiters, Current Opinion in Chemical Biology 13, 678 (2009)). Upon exposure to near-UV light of 365 nm, the NPOM group may be detached, permitting hybridization of an oligonucleotide containing a complementary sequence. For optimal masking properties, NPOM groups should generally be attached every five to six bases apart (see D. D. Young, et al., Chemical Communications 4, 462 (2008)). This group may also be attached to a guanidine, although this modification is generally less commonly used. One or several NPOM-caged bases may be incorporated into the 5' end of the photocaged adapter sequence, which may permit hybridization of linker and barcode strands upon photonic energy exposure at near UV wavelength. Following hybridization, a ligation or click reaction may couple the barcoded strands to the photo-controlled adapter.

Another aspect of the disclosure relates to methods of labeling nucleic acids within a first portion of a plurality of cells. In some embodiments, the methods may include: (a) generating complementary DNAs (cDNAs) within the plurality of cells comprising the first portion by reverse transcribing RNAs using a reverse transcription (RT) primer, (b) exposing the first portion of the plurality of cells to photonic energy to activate a portion of the photo-controlled linkers within the first portion, (c) providing primary nucleic acid tags to the plurality of cells, (d) coupling the activated photo-controlled linkers within the first portion with the provided primary nucleic acid tags, (e) providing secondary nucleic acid tags to the plurality of cells, (f) coupling a portion of the primary nucleic acid tags within the first portion with the secondary nucleic acid tags, and/or (g) exposing the first portion of the plurality of cells to photonic energy to activate a portion of the second photo-controlled linkers within the first portion. In certain embodiments, the methods may further include (h) repeating steps (e), (f), and/or (g) with subsequent nucleic acid tags.

The methods may further include repeating steps (b), (c), and/or (d) with subsequent nucleic acid tags. For example, steps (b), (c), and/or (d) may be repeated a number of times sufficient to generate a unique series of barcode domains within the first portion of the plurality of cells. Steps (b), (c), and/or (d) may be repeated 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, or another suitable number of times. The methods may further include repeating step (h) a number of times sufficient to generate a unique series of barcode domains within the first portion of the plurality of cells. Step (h) may be repeated 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, or another suitable number of times. In certain embodiments, the majority of the nucleic acid tag-bound nucleic acids from the first portion of the plurality of cells may include the same series of bound nucleic acid tags.

In various embodiments, the RT primer may include a first hybridization domain, a domain at least partially complementary to the first hybridization domain, and/or a photo-controlled linker coupling the first hybridization domain and the domain at least partially complementary to the first hybridization domain. In some embodiments, RNA may be reverse transcribed using a photocleavable RT primer. Reverse transcription can be performed through any means and using any reagents known in the art. In certain embodiments, through a series of photonic energy-activated labeling steps, an ROI-specific sequence of DNA oligonucleotides can be attached to the 5' end of the RT primer and thus the cDNA. Subsequently, cells may be lysed, cDNA may be extracted, and RNA may be removed. A 3' adapter sequence may be coupled to the cDNA, and the resulting cDNA products may be PCR amplified and sequenced. The domain at least partially complementary to the hybridization domain can inhibit binding of other nucleic acids to the hybridization domain.

In some embodiments, each or at least a portion of the primary nucleic acid tags may include a domain complementary to the first hybridization domain and/or a primary barcode domain. In certain embodiments, each or at least a portion of the secondary nucleic acid tags may include a secondary barcode domain at least partially complementary to the primary barcode domain, a second hybridization domain, a domain at least partially complementary to the second hybridization domain, and/or a second photo-controlled linker coupling the second hybridization domain with the domain at least partially complementary to the second hybridization domain.

Figure 5:
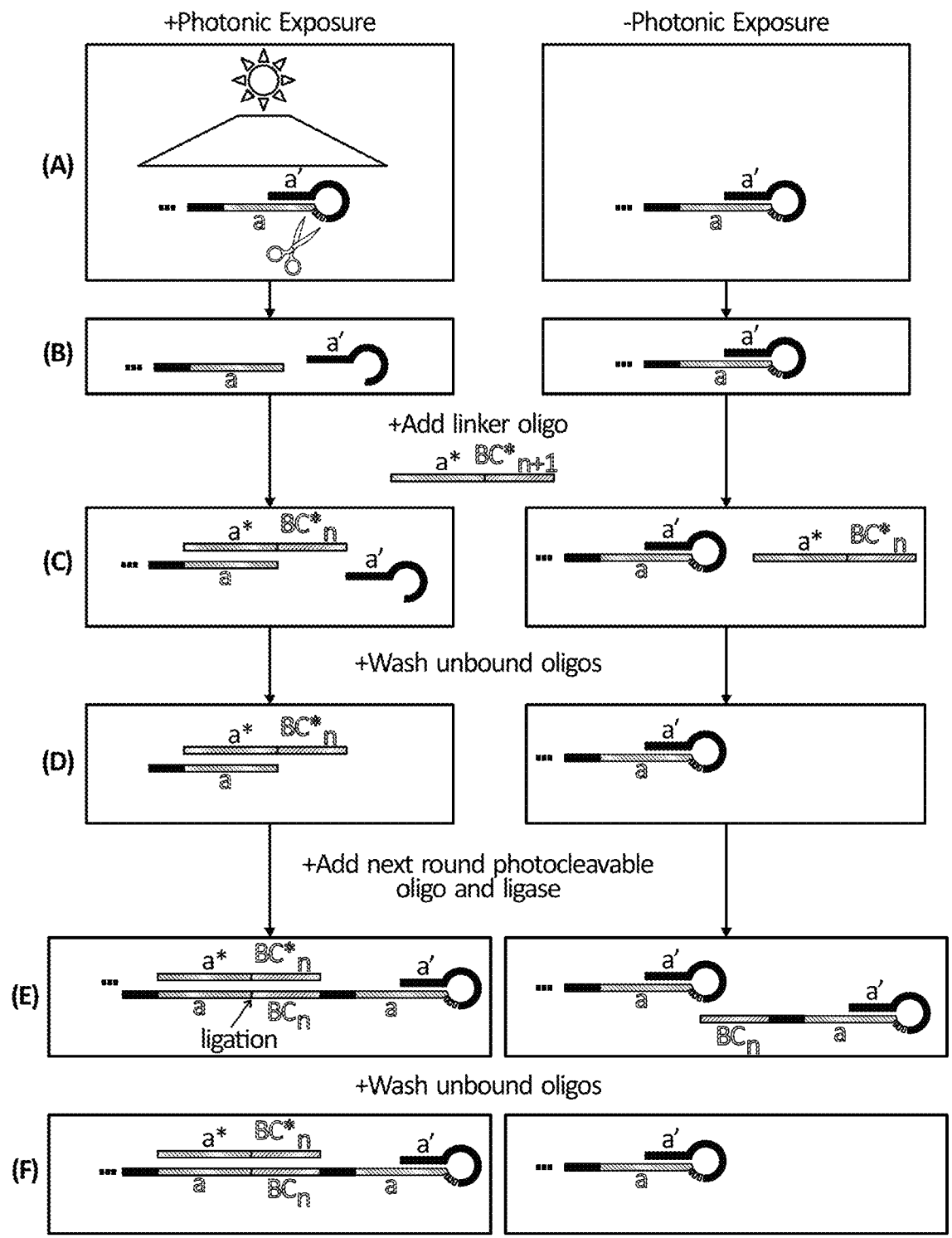
FIG. 5 depicts a comparison of two regions, both exposed to adapter molecules and barcode nucleic acid molecules in which one region is exposed to photonic energy and the other is not.

The methods disclosed herein can be compatible with any of the barcode nucleic acid sequences and linkers depicted in FIG. 2. With reference to FIG. 5, (A) shows that a photocleavable linker that has been previously attached to a nucleic acid within a sample can be exposed to photonic energy at an appropriate wavelength to cleave the photocleavable linker (left) or not exposed to photonic energy (right). (B) shows that the exposed photocleavable linker can break and expose a 5' phosphate group (left), while the unexposed linker can remain intact (right). As domain a' is short (<8 nucleotides), the photocleaved fragment (left) including a' can rapidly disassociate, leaving domain a single-stranded and accessible. (C) shows the addition of a linker oligo having the domain a*, which is complementary to domain a. The linker oligo can hybridize efficiently to domain a after photocleavage (left), but may not bind efficiently to domain a in the uncleaved oligo (right) because domain a' can competitively base pair with domain a. The length of domain a can depend on sequence, but can be in the range of about 6 nucleotide to about 10 nucleotides. (D) shows that wash steps can be performed to remove unbound oligos. (E) shows the addition of a photocleavable linker for the next round with a double-stranded DNA ligase. This ligase can be T4 DNA ligase, T7 DNA ligase, Taq Ligase, or another suitable ligase. Ligation may occur after photocleavage (left), but may not occur without photocleavage (right) as the new photocleavable linker cannot hybridize and there is no accessible phosphate to which to ligate. Further rounds of photo-dependent ligation can be performed, possibly with differently barcoded oligos.

In certain embodiments, a final barcode nucleic acid may be appended to a sample nucleic acid molecule, wherein the barcode nucleic acid molecule includes a capture agent for separating nucleic acid molecules from a heterogeneous, lysed sample. Such capture agents may include a capture agent such as, but not limited to, a 5' biotin. A cDNA labeled with a 5' biotin-including nucleic acid tag may allow or permit the attachment or coupling of the cDNA to a streptavidin-coated magnetic bead. In some other embodiments, a plurality of beads may be coated with a capture strand (i.e., a nucleic acid sequence) that is configured to hybridize to a final sequence overhang of a barcode. In yet some other embodiments, cDNA may be purified or isolated by use of a commercially available kit (e.g., an RNEASY™ kit).

The methods of the present disclosure can label nucleic acid molecules in a region of a sample using photonic energy. FIG. 3 depicts two embodiments of the methods of the present disclosure. In one embodiment (left side), a cDNA molecule can be coupled to a photo-cleavable RT primer at the 5' end (FIG. 3, step 1). The RT primer can include a hybridization domain (a), a domain at least partially complementary to the hybridization domain (a*), and a photocleavable linker linking the hybridization domain and the domain at least partially complementary to the hybridization domain.

A region of the sample can be exposed to photonic energy, thereby cleaving photocleavable linkers in the region. A barcode nucleic acid molecule can be added to the sample, wherein the barcode nucleic acid molecule may include a domain complementary to the hybridization domain and a barcode domain, thereby coupling the barcode nucleic acid molecule to the photocleavable adapter sequence with cloven photocleavable linkers. The barcode nucleic acid molecule can include a sequence that uniquely identifies other nucleic acid molecules to which it is bound. Because nucleic acid molecules within the region have cloven photocleavable linkers they may be capable of binding to the barcode nucleic acid molecules. Accordingly, the regions exposed to photonic energy may be labeled through exposure to photonic energy and a barcode nucleic acid molecule.

This capability can be useful in sequencing nucleic acid molecules in sample. By labeling nucleic acid molecules within a chosen region with the same barcode nucleic acid molecule and associating that barcode with the exposed region, a user can lyse and sequence the sample in bulk and identify those sequenced molecules that include the barcode nucleic acid molecules with the exposed region. In certain embodiments, the sample may be treated with a phosphatase enzyme to remove a phosphate moiety from the terminus of the nucleic acid molecules (see FIG. 3, step 2).

In another embodiment (see FIG. 3, right side) a first barcode nucleic acid molecule, which does not include a photocleavable linker, can be added to the sample (FIG. 3, step 3). The first barcode nucleic acid molecule can include a domain complementary to the hybridization domain, a*, and a barcode domain, BC1*. a* can bind to single-stranded domain a included in the RT primer or adapter nucleic acid molecule, while BC1* is the barcode strand. A first ROI can be exposed to photonic energy, resulting in cleavage of the photocleavable linker in the exposed region (FIG. 3, step 4b and FIG. 4). The cleavage reaction can leave behind a 5' phosphate group compatible with a subsequent ligation reaction. If the photocleavable linker is already present (FIG. 3, step 4b) it can now hybridize to domain a in the RT primer. The barcode nucleic acid molecule including a barcode domain and a photocleavable linker can be added to the cells (FIG. 3, step 5b).

The methods of the present disclosure may include exposing a certain region or certain regions to photonic energy and thereby labeling the certain region(s) with barcode nucleic acid molecules. The regions used in the methods of the present disclosure can be contiguous or non-contiguous. The regions can include one cell, a plurality of cells, or only a portion of cells.

In certain embodiments, multiple regions of the sample are exposed to photonic energy. In various embodiments, the regions do not overlap. In various other embodiments, the regions perfectly or partially overlap. In certain embodiments, including overlapping regions, a first region may occupy only a portion of a second, larger region. In other words, the first region may be a subset of the second region.

Figure 6:
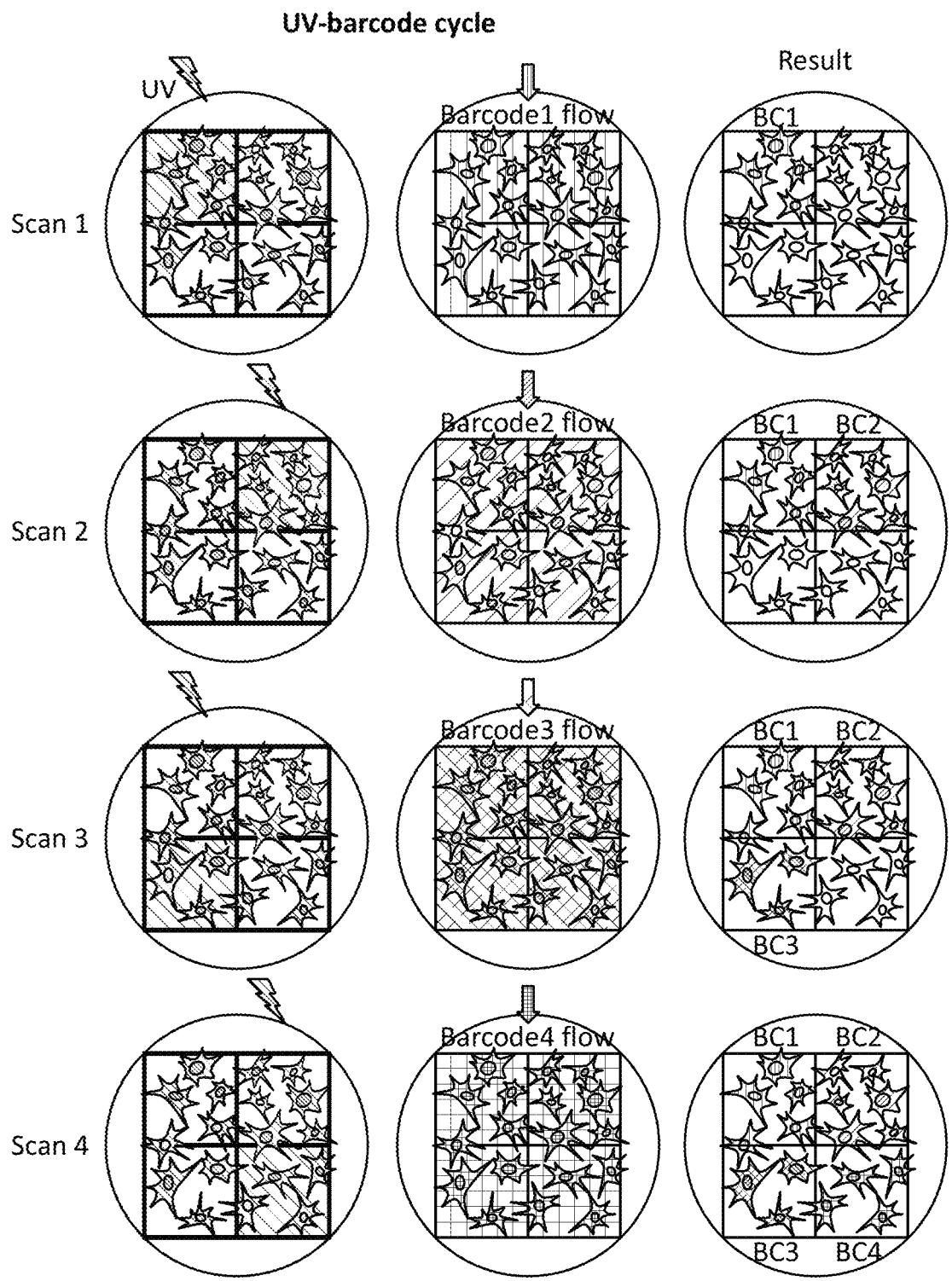
FIG. 6 depicts an embodiment of barcoding or labeling multiple regions of interest (ROIs) from the same sample.
Figure 7:
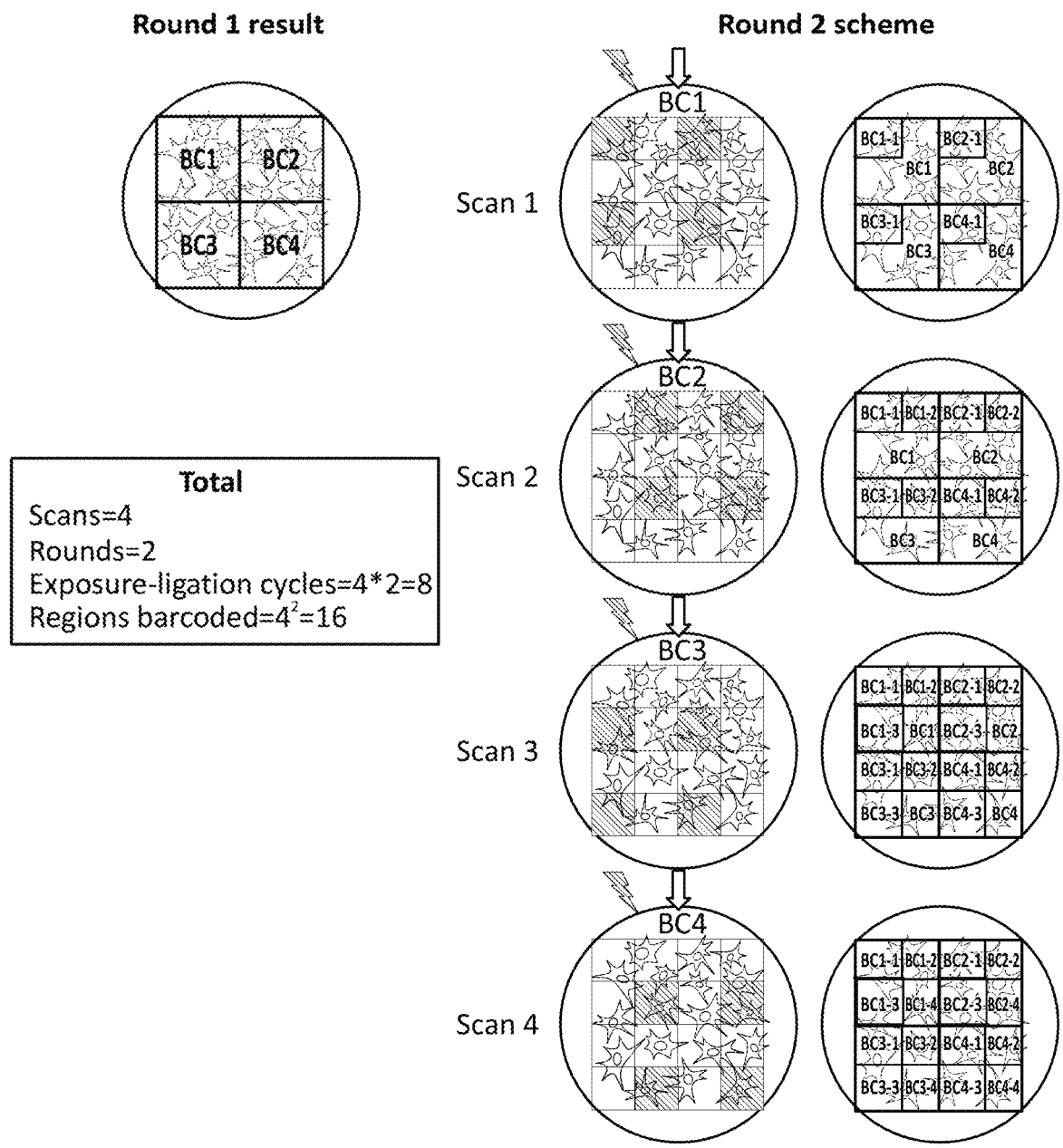
FIG. 7 depicts another embodiment of barcoding multiple ROIs from the same sample.
Figure 8:
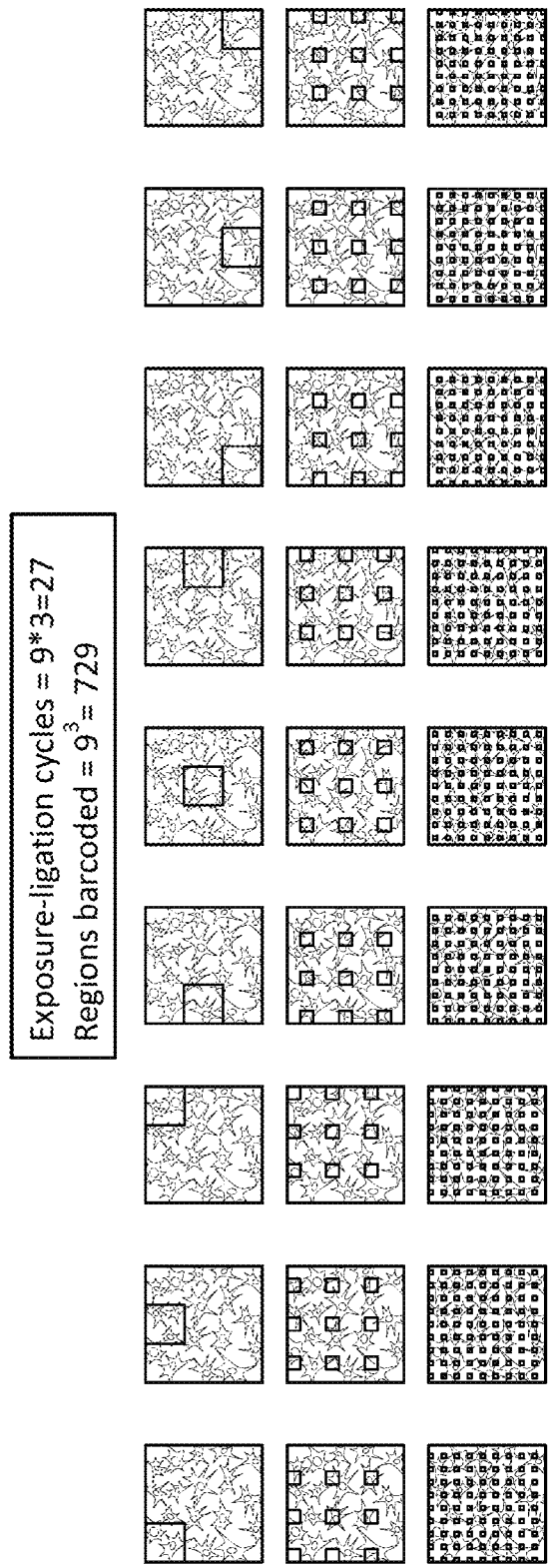
FIG. 8 depicts yet another embodiment of barcoding multiple ROIs from the same sample.
Figure 9:
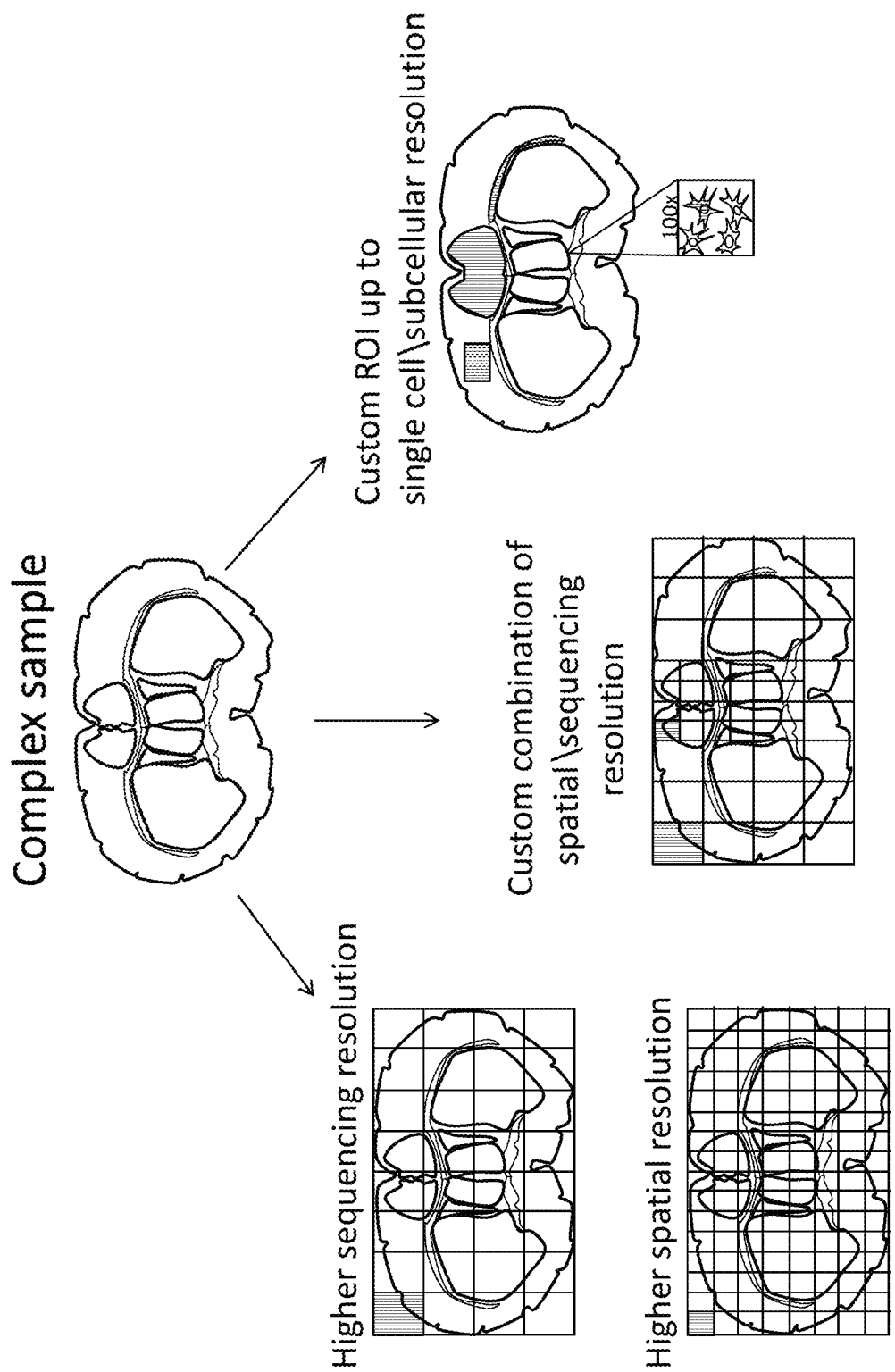
FIG. 9 depicts ways in which regions can be defined in the methods of the present disclosure.

FIG. 6 depicts barcoding multiple regions within a single sample. As depicted, four UV exposure and barcoding steps are used to barcode the cDNAs in four distinct ROIs within the same sample. Each individual step follows the procedure depicted in FIG. 4. FIGS. 7 and 8 depict combinatorial barcoding. Any ROI can be further subdivided to obtain higher spatial resolution. Accordingly, multiple rounds of barcoding can be performed resulting in combinatorial barcodes that uniquely identify each subdivision within the original ROI. FIG. 9 depicts regions imposed in various ways on a biological sample. The spatial resolution, or the number of barcoded regions, may increase exponentially with each additional round. Meanwhile, the labor, time, and/or cost of may only increase linearly with each additional round. For example, as illustrated in FIG. 9, with nine scans and three rounds there are 9×3=27 labeling steps, which can result not in 27, but in $9^3=729$ labeled, or barcoded, regions.

Another aspect of the disclosure relates to kits for labeling molecules within one or more portions of a plurality of cells. In some embodiments, the kit may include a photo-controlled adapter sequence comprising a hybridization domain, a plurality of primary nucleic acid tags comprising a domain complementary to the hybridization domain and a primary barcode domain, and/or a plurality of secondary nucleic acid tags comprising a secondary barcode domain, wherein the primary nucleic acid tags are coupleable to the secondary nucleic acid tags.

In various embodiments, the kits may include one or more of the photo-controlled adapter sequences and/or one or more of the nucleic acid tags as described above. In certain embodiments, the kits may further include one or more additional pluralities of nucleic acid tags. For example, wherein each nucleic acid tag of the one or more additional pluralities of nucleic acids tags comprises a barcode domain. The kits may further include at least one of a phosphatase enzyme, a reverse transcriptase, a fixation agent, a permeabilization agent, a ligation agent, a lysis agent, or another suitable component.

Another aspect of the disclosure relates to systems for labeling molecules within one or more portions of a plurality of cells. In some embodiments, the system may include a reagent depot configured to be in fluid communication with a plurality of cells and/or a photonic energy source configured to expose portions of the plurality of cells to photonic energy.

In various embodiments, the reagent depot may include a first reagent solution. The first reagent solution may include a photo-controlled adapter sequence. The reagent depot may further include a second reagent solution. The second reagent solution may include a plurality of primary nucleic acid tags. The reagent depot may further include a third reagent solution. The third reagent solution may include a plurality of secondary nucleic acid tags. In some embodiments, the primary nucleic acid tags may be coupleable to the secondary nucleic acid tags. The reagent depot may further include a fourth reagent solution, a fifth reagent solution, a sixth reagent solution, or another suitable number of reagent solutions. For example, the fourth reagent solution, the fifth reagent solution, and/or the sixth reagent solution may each include subsequent nucleic acid tags. Additionally, the reagent depot may further include at least one of a reagent solution comprising a phosphatase enzyme, a reverse transcriptase, a fixation agent, a permeabilization agent, a ligation agent, and/or a lysis agent.

In some embodiments, the system may include a stage configured to receive or hold the plurality of cells. In certain embodiments, the system may include a controller operably coupled with at least one of the reagent depot, the photonic energy source, and/or the stage.

In various embodiments, the system may further include a programmable light patterning system operably coupled to the photonic energy source. The programmable light patterning system may include a digital micromirror device (DMD) or another suitable device.

In certain embodiments, the system may further include pumps, tubing, and/or other fluidics devices to deliver reagents, for example, to a stage. In various embodiments, the system may include a plurality of wettably distinct, independent channels capable of sequentially delivering different reagents. The reagents for one or multiple experiments can be stored in the fluidics module, which may also include a cooling element to maintain enzymes and other reagents at suitable temperatures.

Figure 10:
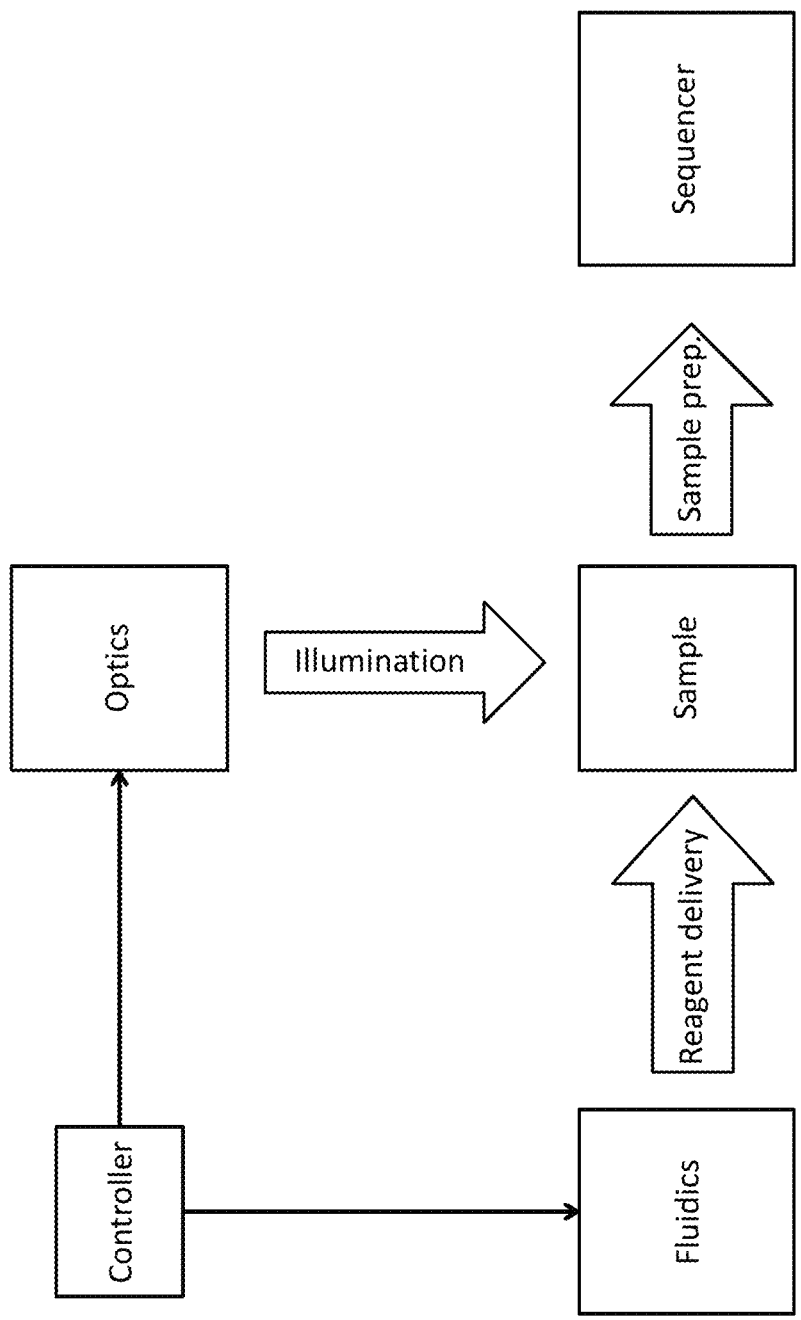
FIG. 10 depicts a schematic of an embodiment of a system for labeling molecules within one or more portions of a plurality of cells.

An optics module may include one or more photonic energy and/or light sources configured to expose regions of a sample to photonic energy and/or light. The photonic energy and/or light source can be a laser, a light-emitting diode (LED), a metal halide lamp, or another suitable light source. In some embodiments, the optics module may further include lenses and/or a DMD for selectively exposing an ROI within the sample with the desired resolution. In some other embodiments, the optics module may include a scanning confocal microscope and/or a mask for illuminating an ROI. FIG. 10 depicts a schematic of an embodiment of a system for labeling molecules within one or more portions of a plurality of cells as disclosed herein.

As will be understood by one of ordinary skill in the art, each embodiment disclosed herein can comprise, consist essentially of, or consist of its particular stated element, step, ingredient, or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient, or component not specified. The transition phrase "consisting essentially of" limits the scope of the embodiment to the specified elements, steps, ingredients, or components, and to those that do not materially affect the embodiment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e., denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the," and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Definitions and explanations used in the present disclosure are meant and intended to be controlling in any future construction unless clearly and unambiguously modified in the following examples or when application of the meaning renders any construction meaningless or essentially meaningless in cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

EXAMPLES

The following examples are illustrative of disclosed methods and compositions. In light of this disclosure, those of skill in the art will recognize that variations of these examples and other examples of the disclosed methods and compositions would be possible without undue experimentation.

Figure 11:
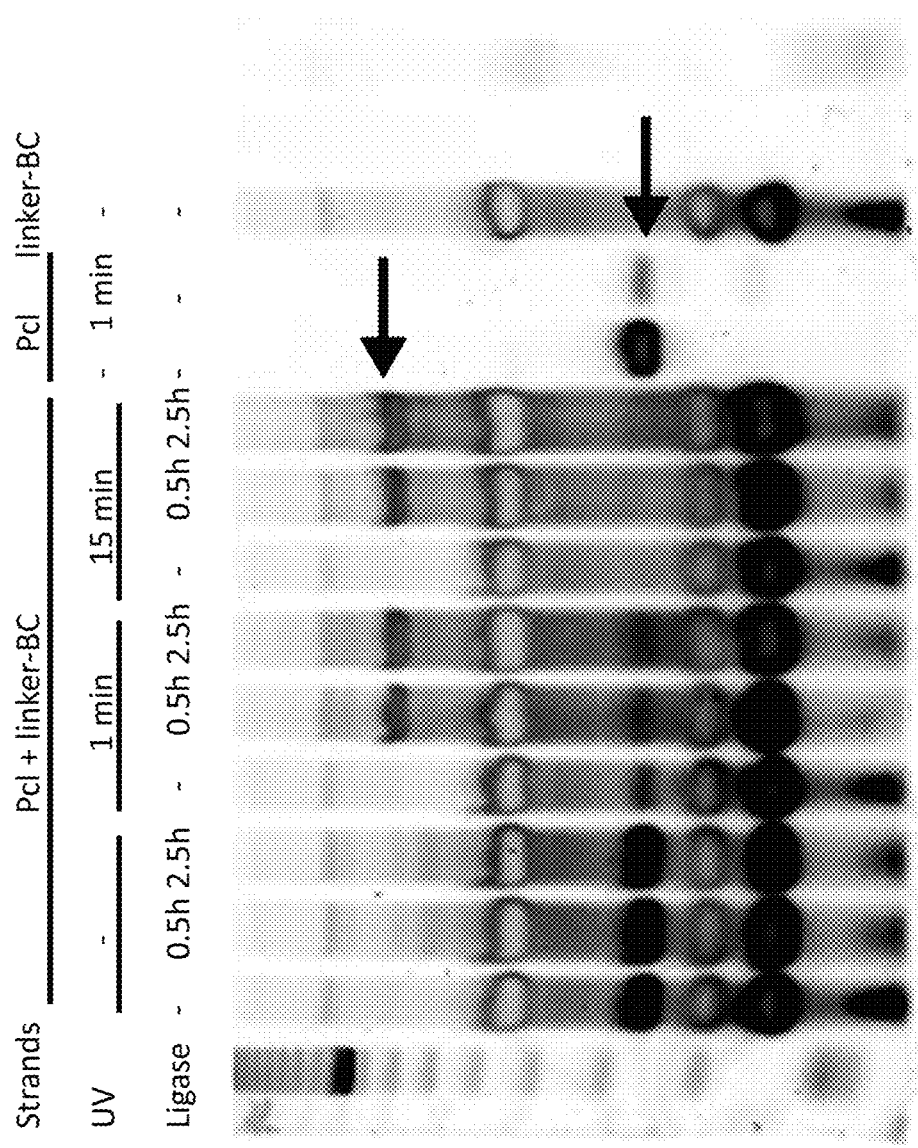
FIG. 11 depicts ligation results after photocleaving a reverse transcription (RT) primer. Exposure to UV light cleaves off a 5'-terminal fragment of the RT primer, leaving behind the terminal phosphate and enabling ligation to the linker-BC complex. The upper arrow points to the ligation products, and the lower arrow points to the photocleavable RT primer (Pcl).

Example 1—Photocleavable Spacer UV-Induced Cleavage and Barcode Ligation In Vitro An RT primer including a photocleavable spacer (see SEQ ID NO:3 in Table 1 below) was exposed to UV light in a transilluminator (MULTIDOC-IT™ Imaging System, UVP™) at 302 nm on high (8 W) for varying times (1 minute, 15 minutes). This primer was then added to a ligation mix including T4 DNA ligase (NEB™) in a specified buffer and a pre-annealed complex of a linker and a biotinylated barcode oligo (Test oligo, Test linker, Table 1). The ligation reaction was allowed to proceed for either 0.5 or 2.5 hours at 37° C. The resulting products were then run on a 10% polyacrylamide gel (see FIG. 11). The appearance of the ligated products can be observed after a 1 minute exposure and a 30 minute ligation time. No products formed and the photocleavable RT primer was stable in the absence of illumination.

TABLE 1

Oligonucleotide Sequences (Barcoding 4 samples with a combination of 2 barcode sequences)

| Name | Sequence |
| --- | --- |
| Test linker | GGGTGAGCTTCACTGTCCATCTG (SEQ ID NO: 1) |
| Test oligo | /5Biosg/ GCTGAACCGCTCTTCCGATCTATCACGNNNNNNNN NNNCAGATGGACAGTGAA (SEQ ID NO: 2) |
| RT primer, photo-cleavable | GTGAGCAAAA/iSpPC/ GCTCACCCTTTTTTTTTTTTTTVN (SEQ ID NO: 3) |
| Barcode1-round2 | /5Biosg/ GCTGAACCGCTCTTCCGATCTNNNNNNNNNNNCA GATGGATCACGTT (SEQ ID NO: 4) |
| Linker1 | GGGTGAGCAACGTGATCCATCTG (SEQ ID NO: 5) |
| Barcode2-round2 | /5Biosg/ GCTGAACCGCTCTTCCGATCTNNNNNNNNNNNCA GATGGGATCAGCG (SEQ ID NO: 6) |
| Linker2 | GGGTGAGCCGCTGATCCCATCTG (SEQ ID NO: 7) |
| Barcode1-PC (round1) | GTGAGCAAAA/iSpPC/ GCTCACCCCAGATGGATCACGTT (SEQ ID NO: 8) |
| Barcode2-PC (round1) | GTGAGCAAAA/iSpPC/ GCTCACCCCAGATGGGATCAGCG (SEQ ID NO: 9) |
| 4xNPOM-caged dT adapter | P~CTCTGTCTTTTTTTTTTTTTTVN (SEQ ID NO: 10) |
| GAPDH forward qPCR primer | CTGGTATGACAACGAATTTGGC (SEQ ID NO: 11) |
| Barcode reverse qPCR primer | CAGACGTGTGCTCTTCCGATCT (SEQ ID NO: 12) |

Table 1 includes the sequences of primers and oligos used in the experiments described herein. N stretches in the barcodes represent the Unique Molecular Identifiers for each original transcript to correct for amplification bias. As used in Table 1, "5Biosg" is biotin, "iSpPC" is a photocleavable spacer (IDT™), 4×NPOM-caged dTs are shown in bold (TRILINK™), and P~ indicates a terminal phosphate.

Figure 12:
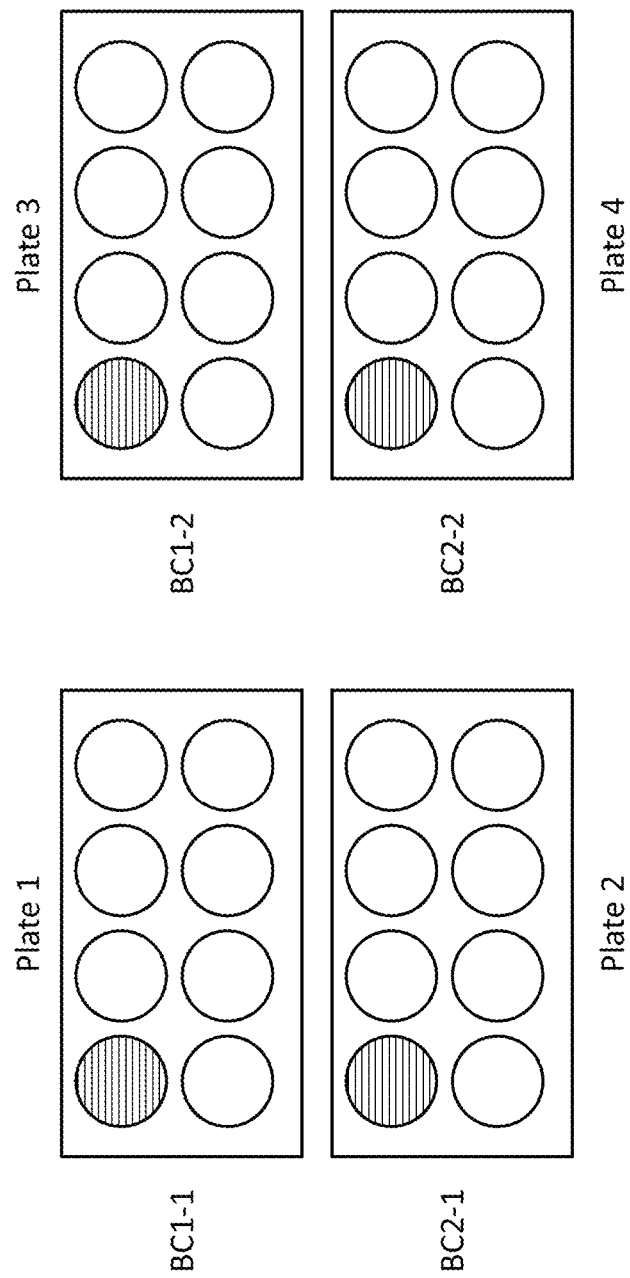
FIG. 12 graphically depicts an experimental setup showing a sample arrangement between four separate cell culture plates. Each sample can be barcoded with a combination of two distinct barcodes BC1 and BC2.

In order to test the combinatorial barcoding scheme provided herein, four distinct samples were labeled using only two different barcode sequences by employing a two scans and two rounds strategy. In order to have independent control over illumination of every individual sample, each of the samples was placed into its own well in four separate 24-well cell culture plates (see FIG. 12).

The samples in this experiment consisted of an adherent layer of HeLa S3 cells (ATCC® CCL-2.2™) growing in each of the wells. The cells, in a near-confluent monolayer, were washed with PBS, fixed in 4% formaldehyde, permeabilized with TRITON™ X-100, and treated with 0.1 N HCl. Following fixation and permeabilization, in situ reverse transcription was set up and left to proceed overnight at 37° C. in the dark with M-MuLV reverse transcriptase and anchored poly-T RT primer containing the photocleavable spacer modification (see Table 1).

Figure 13:
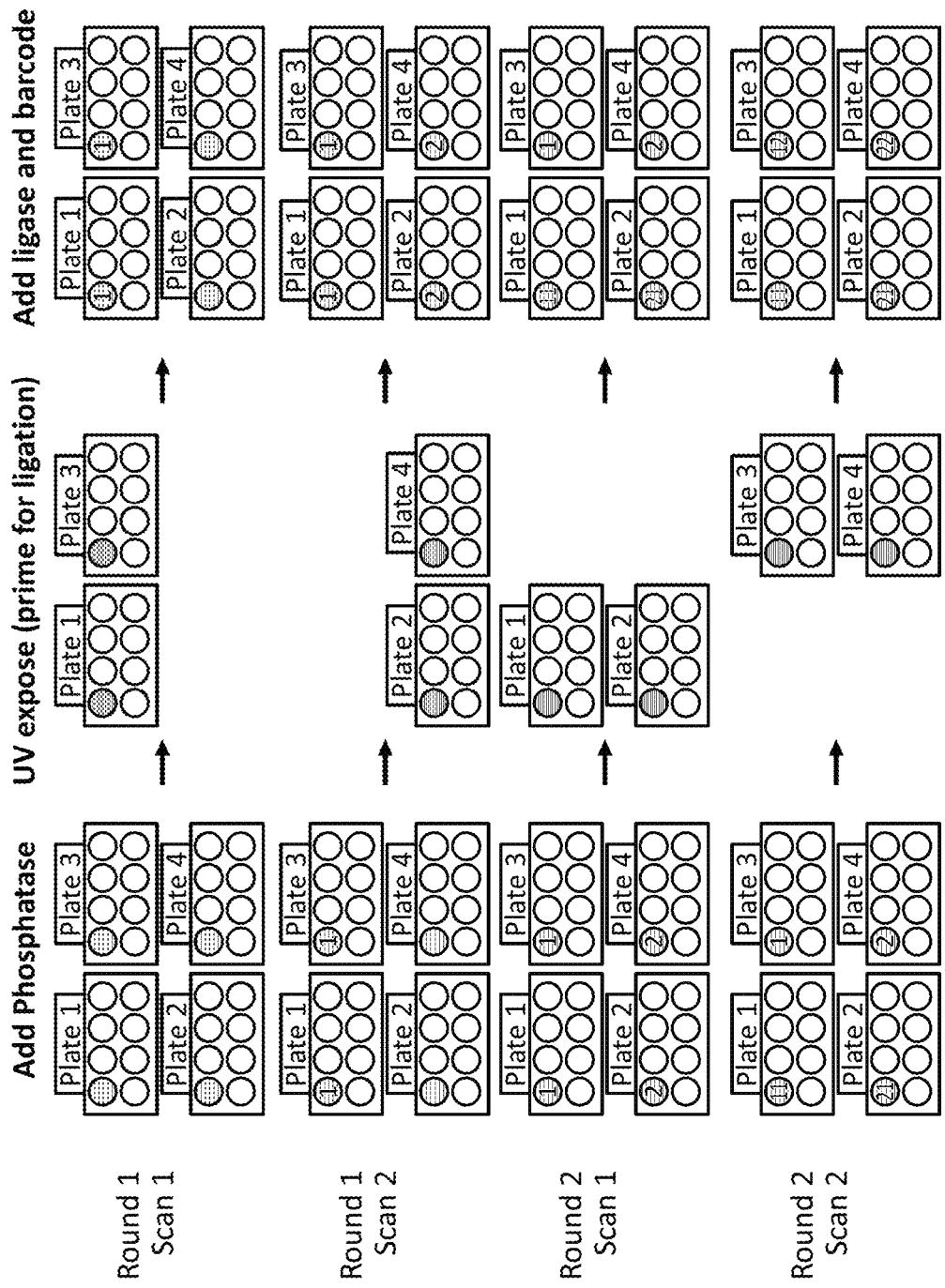
FIG. 13 graphically depicts a combinatorial labeling scheme. During each cycle, all samples receive identical phosphatase treatment to remove background phosphates and prevent unwanted ligation. Then the linker is added to all samples (not shown) and a subset of samples is illuminated with UV light in a pattern specific for each cycle. Light (or photonic energy) exposes a terminal phosphate in the illuminated samples, permitting barcode ligation in the subsequent step. Although in the next step barcode and ligase solution is added to all samples, only the samples illuminated in the previous step will be able to attach the barcode. For clarity, wash steps between all steps are not shown.

The next day, the combinatorial labeling scheme comprised of a series of phosphatase treatments, UV exposures, barcode ligations, and wash steps was conducted. Antarctic Phosphatase and T4 DNA ligase from NEB™ were used. All samples received the same chemical treatments at all steps, as if they were sharing a common environment, but only a subset of samples was illuminated during each cycle (see FIG. 13).

For each labeling cycle, all steps were carried out in the dark except the illumination step. The samples were first washed with water and then treated with phosphatase for 15 minutes. Following a water wash, a linker solution specific for the cycle was added to all samples, and a subset of samples was illuminated for five minutes in a UV transilluminator. The specific linker in high concentration (2 μM) was added prior to illumination to ensure that after photo-cleavage the exposed complementary region with a phosphate would not be primarily occupied by a carried-over linker-barcode from the previous cycle. Immediately after illumination, a solution containing ligase and a cycle-specific barcode (see Table 1) was added to all samples and they were incubated for 30 minutes. After ligation, two formamide washes (50% formamide) were performed to remove any unbound linker and barcode, followed by a water wash. The final (round 2) barcodes carried biotin at the 5' end to facilitate purification of the barcoded product.

After four cycles of barcode labeling, all samples were lysed and incubated with streptavidin beads (DYNABEADS® MYONE™ Streptavidin C1) to purify barcoded cDNA. After washing and RNAse-treating the beads, 3'-adapter ligation (T4 RNA ligase, NEB™) was performed on the cDNA bound to the beads.

Finally, sequencing products were generated by performing 10 cycles of PCR with the bead-immobilized cDNA, extracting the supernatant with 0.6× AMPURE™ XP beads (AGENCOURT™), and repeating the PCR-extraction steps to purify the DNA from adapter self-ligation product. The final product was run on a 1.5% agarose gel and the DNA fragment roughly corresponding to a 500 bp band was extracted. During the PCR steps, sequencing adapters including a sample index (identifying which plate the sample came from) were added to each end of the cDNA fragment. The resulting product was sequenced on a MISEQ™ sequencer (ILLUMINA®).

Figure 14:
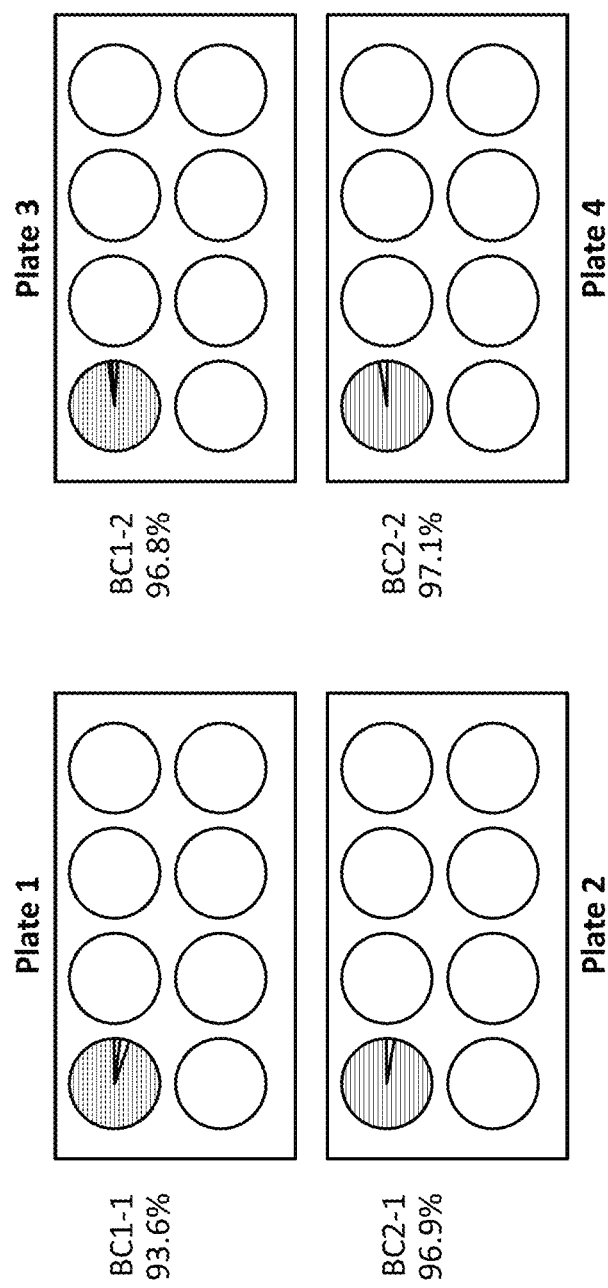
FIG. 14 graphically depicts the results of a barcoding experiment comprising two scans and two rounds. The pie charts show the fractions of reads harboring one of the four different combinations of barcodes (BC1-1, BC1-2, BC2-1, or BC2-2) for each sample.

The sequencing run produced about 2.7 million reads which were sorted according to the sample index to identify all four samples. For each sample, the fraction of reads with each combination of barcodes was calculated (see FIG. 14).

The barcoding scheme resulted in high specificity, correctly identifying 94-97% of cells in every sample by the combination of attached barcodes.

Example 2—In Vitro Barcode Ligation to a Photocleavable Adapter Sequence

FIG. 15A depicts one round of in vitro barcode ligation in a specifically illuminated region of a sample including a photocleavable adapter sequence. Nucleic acid species in both wells of a petri dish insert on the microscope stage: a photocleavable adapter and two hybridized barcode strands. Upon UV exposure and addition of ligase, the cleaved photocleavable adapter sequence can be ligated to the barcode strands. FIG. 15B depicts a schematic of the experiment. Both wells contained the same nucleic acid species, and well 1 was exposed with 405 nm light with a 10× objective at 50% power, 100 iterations via a confocal microscope. The ligase was then added and the reaction proceeded for one hour at 37° C. FIG. 15C is a polyacrylamide gel showing the appearance of the ligation product in well 1.

Example 3—In Vitro Barcode Ligation to a Photocaged Adapter Sequence

FIG. 16A illustrates one round of in vitro barcode ligation to a photocaged adapter sequence. Nucleic acid species in both wells of a petri dish insert on the microscope stage: an 8 base pair adapter featuring four evenly spaced NPOM-caged dT residues and a terminal phosphate (see SEQ ID NO:10 in Table 1) and two hybridized barcode strands. Upon UV exposure, the photo-uncaged adapter hybridized to the complementary region of the forward barcode strand. When the ligase was added, the adapter was ligated to the barcode strands.

FIG. 16B is a schematic of the experiment. Both test tubes contained the same nucleic acid species, and Sample 2 was exposed to UV light via a transilluminator (MULTIDOC-IT™ Imaging System, UVP™) at 302 nm on high (8 W) for two minutes. The ligation was allowed to proceed for one hour at 37° C. FIG. 16C is a polyacrylamide gel showing the appearance of the ligation product (adapter+barcode) in Sample 2.

Example 4—Barcode Ligation in HeLa Cells

Figure 17A:
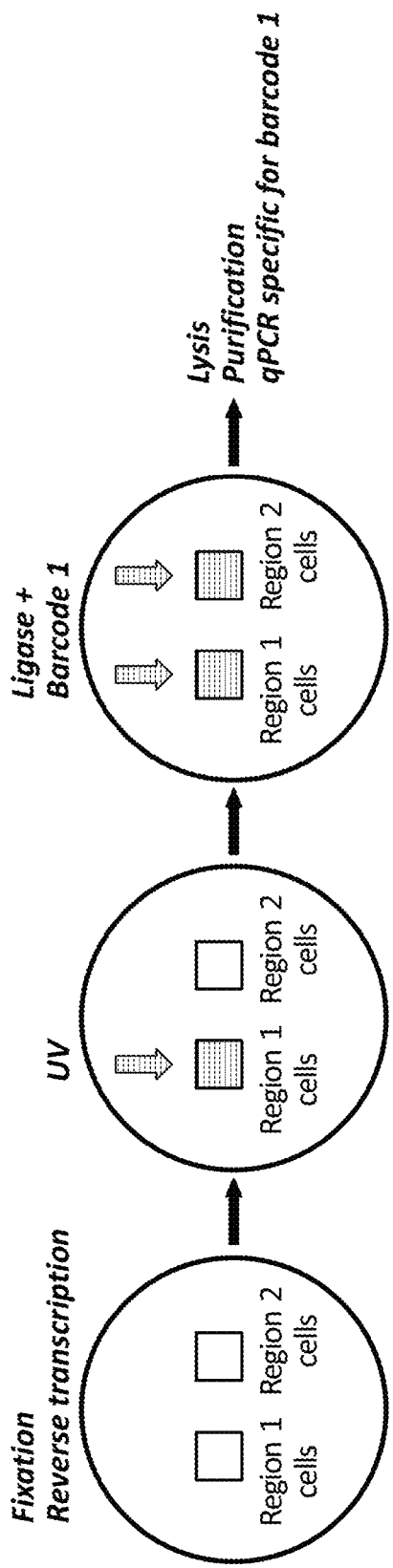
FIG. 17A is a schematic depicting an experiment to assay for the presence of barcode ligation product.
Figure 17B:
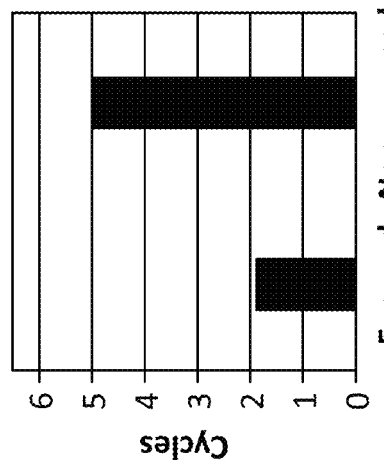
FIG. 17B is a graph showing qPCR results from the experiment depicted in FIG. 17A.

FIG. 17A is a schematic of the experiment described herein. HeLa cells were seeded into a petri dish with a silicone insert defining two regions. The cells were fixed, permeabilized, and the RNA in the cells was reverse transcribed into cDNA. Then, Region 1 was exposed to 405 nm light with a 10× objective at 50% power, 200 iterations via confocal microscope, and barcode and ligase solution was added to the dish. The ligation was allowed to proceed for one hour at 37° C. Following cell lysis, nucleic acids were extracted and the presence of the barcode ligation product was assayed by qPCR with primers specific to the barcode and GAPDH gene as a reference (see Table 1 for primer sequences). FIG. 17B depicts the qPCR result showing the barcoded products in exposed and non-exposed regions.

Example 5—Method of Labeling Molecules within a Portion of a Plurality of Cells

Figure 18:
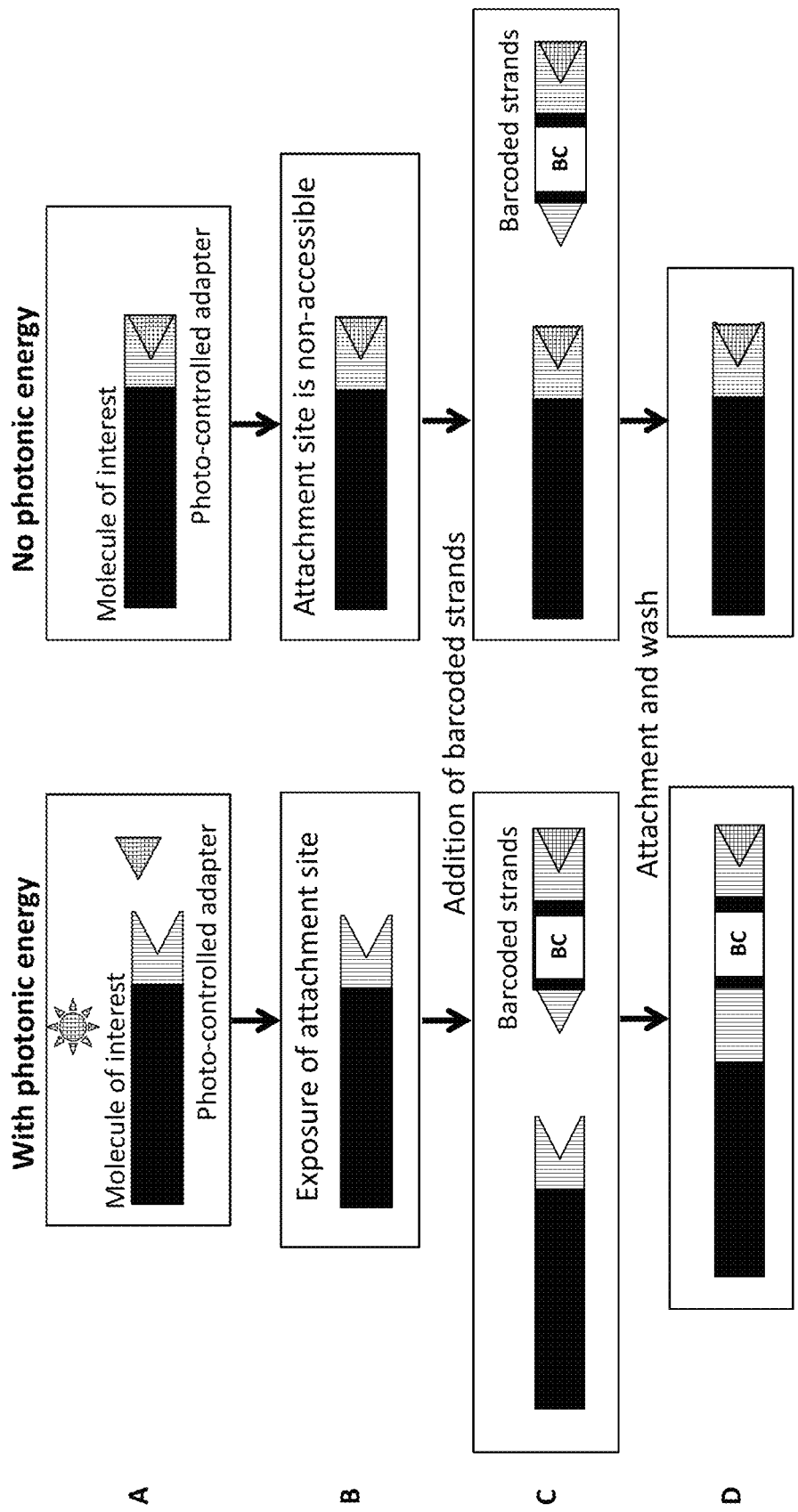
FIG. 18 depicts an embodiment of a method of labeling molecules within one or more portions of a plurality of cells.

Step A of FIG. 18 depicts a molecule of interest, such as an mRNA/cDNA hybrid strand, with a photo-controlled adapter sequence that has been previously attached to it within a sample. The molecule can be either subjected to photonic energy at the appropriate wavelength to activate the adapter and expose its active end domain (left) or not subjected to photonic energy (right).

Upon exposure, as illustrated at step B, the 5' end domain may become accessible. Step C illustrates addition of barcoded strands that may be able to attach to the exposed end domain of the photo-controlled adapter. They may (as illustrated) or may not include a photo-controlled domain attached to an opposing end. In the former case, further rounds of photo-controlled barcode attachments can be performed, possibly with differently barcoded strands. In the latter case, further rounds of barcode additions may not be possible. The barcoded strands can become covalently attached to the end domain that has been activated with photonic energy (left). Wash steps may be performed to remove unbound strands.

Example 6—Counteracting Off-Target Illumination

Figure 19:
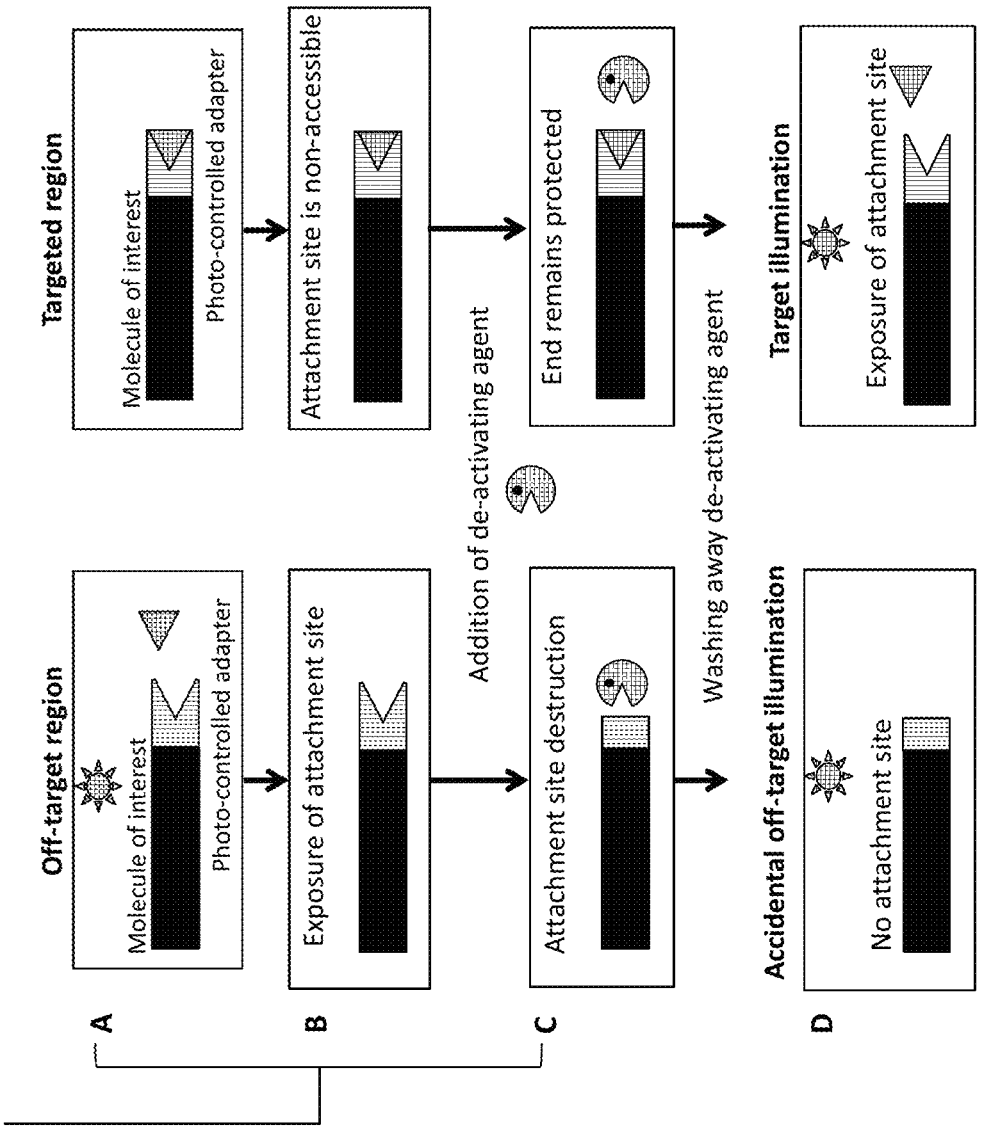
FIG. 19 depicts an embodiment of a method of pre-processing a plurality of cells.

As shown in FIG. 19, a "blackout" pre-processing strategy (i.e., Steps A-C) for counteracting accidental off-target illumination and reducing background barcoding of non-targeted regions may be performed. Step A depicts a molecule, such as an mRNA/cDNA hybrid strand, with a photo-controlled adapter sequence that has been previously attached to it within a sample. As a pre-processing step, the molecule in the off-target region can be subjected to photonic energy at the appropriate wavelength to expose the adapter's active end domain (left) or left not subjected to photonic energy in the targeted region (right). Upon exposure, as shown in Step B, the end domain attachment site can become accessible. As shown in Step C, an agent capable of de-activating the attachment site may be added. This can result in the destruction of the exposed attachment site in the off-target region, which cannot be further regained for barcoding. The attachment site in the targeted region is protected. After the de-activating agent is washed away, as shown in Step D, both areas in the sample may be ready for barcoding with reduced background signal due to the loss of attachment site in the off-target region.

Example 7—a Pre-Processing Step for Counteraction of Off-Target Illumination

Figure 20:
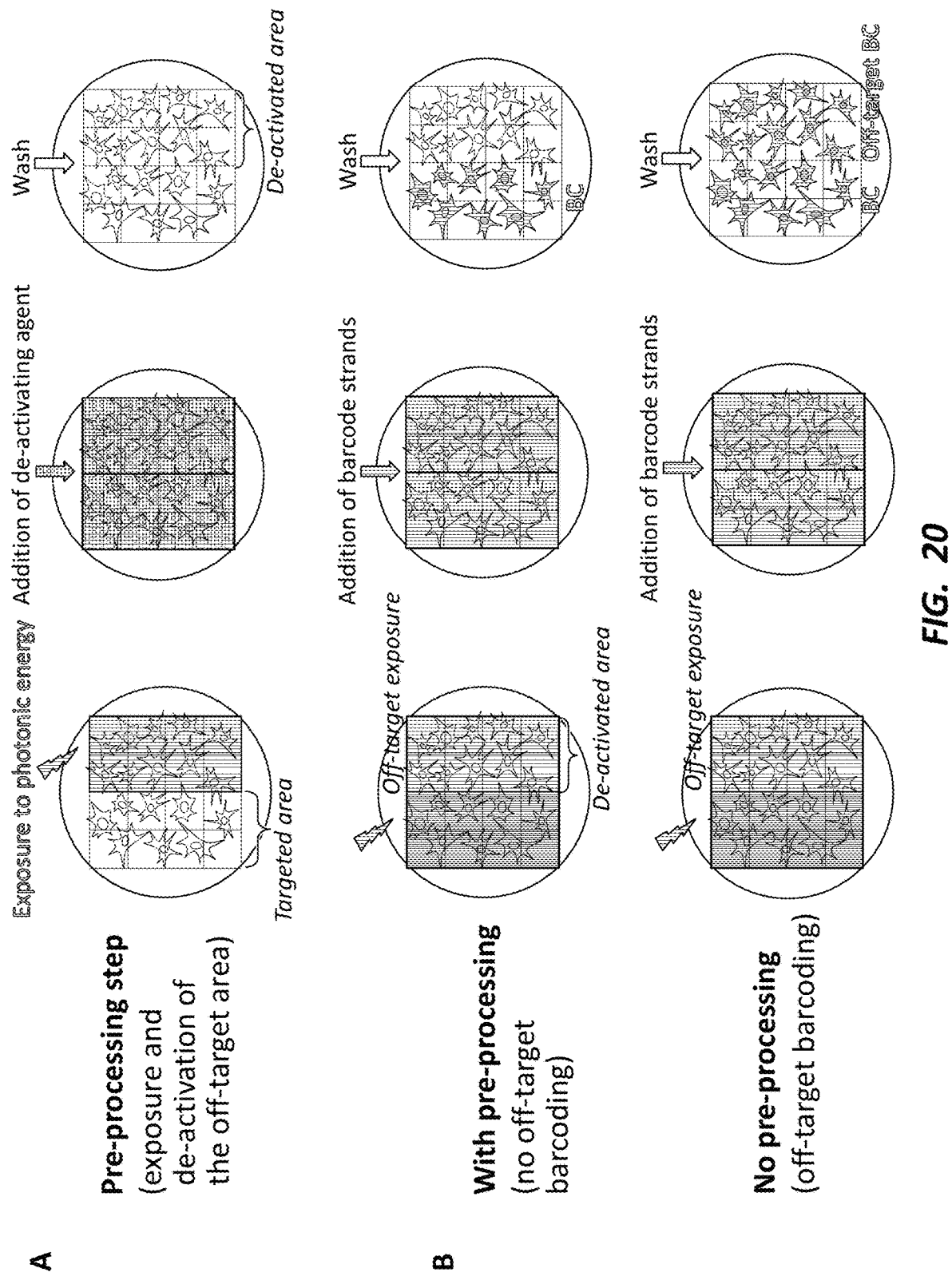
FIG. 20A depicts a method of applying a pre-processing step to counteract off-target exposure of a plurality of cells, in accordance with an embodiment of the disclosure.
FIG. 20B depicts the spatial precision of barcoding with and without the pre-processing step, in accordance with an embodiment of the disclosure.

FIG. 20 depicts that a pre-processing step can be applied for counteracting accidental off-target illumination to the sample. "A" depicts a pre-processing treatment. The off-target region, which is not intended for barcoding, can be subjected to photonic energy at the appropriate wavelength ("A," left). Upon exposure, the end domain attachment site may become accessible. A de-activating agent ("A," middle) can be added to the sample after the reaction is washed away. This can result in the destruction of the exposed attachment site in the off-target region creating a de-activated area within the sample that cannot be barcoded.

Due to potential background illumination effects, some molecules within the original target area may also get de-activated. However, this may generally only affect the efficiency of capturing the molecules within the target area, whereas omitting the pre-processing step might undermine the precision of assigning each barcode to a specified region and therefore limit spatial resolution of the barcoding. "B" depicts the spatial precision of barcoding with and without the pre-processing step as shown in "A."

Following the pre-processing treatment, the subsequent target area's exposure to photonic energy and addition of the barcode strands can result in the attachment of barcode strands only in the target region where the attachment site is still intact (upper panel), even if some areas outside the target region receive off-target illumination, for example, as a result of light scattering or reflection. In the absence of the pre-processing step, off-target illumination can result in background attachment of barcodes within other areas of the sample not intended to be barcoded in this step (lower panel).

Certain embodiments of this disclosure are described herein, including the best mode known to the inventors for carrying out the disclosure. Of course, variations on these described embodiments will become apparent to those of ordinary skill in the art upon reading the foregoing description. The applicants expect skilled artisans to employ such variations as appropriate, and the applicants intend for the various embodiments of the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Furthermore, numerous references have been made to patents and printed publications throughout this specification. Each of the above-cited references and printed publications are individually incorporated herein by reference in their entirety.

It is to be understood that the embodiments of the present disclosure are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

The particulars shown herein are by way of example and for purposes of illustrative discussion of the preferred embodiments of the present disclosure only and are presented in the cause of providing what is believed to be the most useful and readily understood description of the principles and conceptual aspects of various embodiments of the disclosure.

It will be apparent to those having skill in the art that many changes may be made to the details of the above-described embodiments without departing from the underlying principles of the disclosure. The scope of the present invention should, therefore, be determined only by the following claims.

The invention claimed is:

1. A method of labeling molecules within one or more portions of a plurality of cells, the method comprising:
   (a) coupling at least one photo-controlled adapter sequence to molecules within the plurality of cells;
   (b) exposing a first portion of the plurality of cells to photonic energy to activate the at least one photo-controlled adapter sequence within the first portion of the plurality of cells;
   (c) providing primary nucleic acid tags to the plurality of cells;
   (d) coupling the activated photo-controlled adapter sequences within the first portion of the plurality of cells with the provided primary nucleic acid tags;
   (e) exposing a second portion of the plurality of cells to photonic energy to activate the at least one photo-controlled adapter sequence and/or the primary nucleic acid tags within the second portion of the plurality of cells;
   (f) providing secondary nucleic acid tags to the plurality of cells;
   (g) coupling the activated photo-controlled adapter sequence and/or the activated primary nucleic acid tags within the second portion of the plurality of cells with the provided secondary nucleic acid tags, and
   (h) permeabilizing at least a portion of the plurality of cells to nucleic acids and polypeptides prior to step (a).

2. The method of claim 1, further comprising:
   repeating steps (b), (c), and (d) with subsequent nucleic acid tags and within subsequent portions of the plurality of cells, wherein steps (b), (c), and (d) are repeated a number of times sufficient to generate a unique series of nucleic acid tags for the molecules within a specific portion of the plurality of cells.

3. The method of claim 1, further comprising:
   (i) repeating steps (e), (f), and (g) with subsequent nucleic acid tags and within subsequent portions of the plurality of cells, wherein step (i) is repeated a number of times sufficient to generate a unique series of nucleic acid tags for the molecules within a specific portion of the plurality of cells.

4. The method of claim 3, wherein the number of times is selected from 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, and 100.

5. The method of claim 3, wherein the majority of the nucleic acid tag-bound nucleic acids from the specific portion of the plurality of cells comprise the same series of bound nucleic acid tags.

6. The method of claim 1, further comprising:
identifying a portion of the plurality of cells having molecules that are not to be labeled;
exposing the identified portion of the plurality of cells to photonic energy prior to step (b); and
treating the plurality of cells with an agent that deactivates the photo-controlled adapter sequence, wherein the agent is at least one of a phosphatase, a specific oligonucleotide to be filtered out, a blocking oligonucleotide having a higher binding energy to the photo-controlled adapter sequence than the nucleic acid tags, an enzyme that specifically destroys or modifies an uncaged sequence, and a protein that binds to an exposed specific protein binding site.

7. The method of claim 1, wherein the photo-controlled adapter sequence is a photocaged adapter sequence comprising a hybridization domain, the hybridization domain comprising one or more photocaged nucleic acids.

8. The method of claim 1, wherein the photo-controlled adapter sequence is a photocleavable adapter sequence comprising:
a hybridization domain;
a domain at least partially complementary to the hybridization domain; and
a photocleavable linker coupling the hybridization domain and the domain at least partially complementary to the hybridization domain.

9. The method of claim 1, further comprising:
treating the plurality of cells with an agent that deactivates the photo-controlled adapter sequence prior to step (b), wherein the agent is at least one of a phosphatase, a specific oligonucleotide to be filtered out, a blocking oligonucleotide having a higher binding energy to the photo-controlled adapter sequence than the nucleic acid tags, an enzyme that specifically destroys or modifies an uncaged sequence, and a protein that binds to an exposed specific protein binding site.

10. The method of claim 1, further comprising:
fixing the plurality of cells prior to step (a).

11. The method of claim 1, wherein the plurality of cells is selected from a portion of at least one of a mammal, a plant, a *Danio* species, a *Drosophila* species, a *Caenorhabditis* species, and a bacterium.

12. The method of claim 1, wherein the molecules are selected from at least one of RNA, cDNA, DNA, protein, peptide, and antigen.

13. A method of labeling nucleic acids within a first portion of a plurality of cells, the method comprising:
(a) generating complementary DNAs (cDNAs) within the plurality of cells comprising the first portion by reverse transcribing RNAs using a reverse transcription primer, the reverse transcription primer comprising:
a first hybridization domain;
a domain at least partially complementary to the first hybridization domain; and
a photo-controlled linker coupling the first hybridization domain and the domain at least partially complementary to the first hybridization domain;
(b) exposing the first portion of the plurality of cells to photonic energy to activate a portion of the photo-controlled linkers within the first portion;
(c) providing primary nucleic acid tags to the plurality of cells, wherein each of the primary nucleic acid tags comprises:
a domain complementary to the first hybridization domain; and
a primary barcode domain;
(d) coupling the activated photo-controlled linkers within the first portion with the provided primary nucleic acid tags;
(e) providing secondary nucleic acid tags to the plurality of cells, wherein each of the secondary nucleic acid tags comprises:
a secondary barcode domain at least partially complementary to the primary barcode domain;
a second hybridization domain;
a domain at least partially complementary to the second hybridization domain; and
a second photo-controlled linker coupling the second hybridization domain with the domain at least partially complementary to the second hybridization domain;
(f) coupling a portion of the primary nucleic acid tags within the first portion with the secondary nucleic acid tags;
(g) exposing the first portion of the plurality of cells to photonic energy to activate a portion of the second photo-controlled linkers within the first portion;
(h) repeating steps (e), (f), and (g) with subsequent nucleic acid tags, and
(i) permeabilizing at least a portion of the plurality of cells to nucleic acids and polypeptides prior to step (a).

14. The method of claim 13, further comprising:
repeating steps (b), (c), and (d) with subsequent nucleic acid tags, wherein steps (b), (c), and (d) are repeated a number of times sufficient to generate a unique series of barcode domains within the first portion of the plurality of cells.

15. The method of claim 13, wherein step (h) is repeated a number of times sufficient to generate a unique series of barcode domains within the first portion of the plurality of cells, wherein the number of times is selected from 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, and 100.

16. The method of claim 13, wherein at least one of the reverse transcription primer and the secondary nucleic acid tags further comprises a second photocleavable linker.

17. The method of claim 13, further comprising:
treating the plurality of cells with an agent that deactivates the photo-controlled linkers prior to step (b), wherein the agent is at least one of a phosphatase, a specific oligonucleotide to be filtered out, a blocking oligonucleotide having a higher binding energy to the photo-controlled adapter sequence than the nucleic acid tags, an enzyme that specifically destroys or modifies an uncaged sequence, and a protein that binds to an exposed specific protein binding site.

18. The method of claim 13, further comprising:
fixing the plurality of cells prior to step (a).

19. The method of claim 13, wherein the plurality of cells is selected from a portion of at least one of a mammal, a plant, a *Danio* species, a *Drosophila* species, a *Caenorhabditis* species, and a bacterium.

* * * * *